United States Patent
Mocny

(10) Patent No.: US 11,116,791 B2
(45) Date of Patent: Sep. 14, 2021

(54) COMPOSITIONS AND METHODS FOR THE TREATMENT OF CYSTIC FIBROSIS

(71) Applicant: RDG Holdings, Inc., Pleasant Grove, UT (US)

(72) Inventor: Jeffrey Mocny, Durham, NC (US)

(73) Assignee: RDG HOLDINGS, INC., Pleasant Grove, UT (US)

( * ) Notice: Subject to any disclaimer, the term of this patent is extended or adjusted under 35 U.S.C. 154(b) by 0 days.

(21) Appl. No.: 16/126,193

(22) Filed: Sep. 10, 2018

(65) Prior Publication Data

US 2019/0328776 A1 Oct. 31, 2019

Related U.S. Application Data

(60) Provisional application No. 62/662,325, filed on Apr. 25, 2018.

(51) Int. Cl.
*A61K 33/20* (2006.01)
*A61K 45/06* (2006.01)
*A61K 9/08* (2006.01)
*A61P 31/04* (2006.01)

(52) U.S. Cl.
CPC ............... *A61K 33/20* (2013.01); *A61K 9/08* (2013.01); *A61K 45/06* (2013.01); *A61P 31/04* (2018.01)

(58) Field of Classification Search
CPC .......... A61K 33/20; A61K 9/08; A61K 45/06; A61P 31/04
See application file for complete search history.

(56) References Cited

U.S. PATENT DOCUMENTS

| | | | |
|---|---|---|---|
| 2006/0073212 A1* | 4/2006 | Palmer | A61K 33/20 424/600 |
| 2015/0196590 A1* | 7/2015 | Sampson | A61K 33/20 424/445 |
| 2016/0317577 A1* | 11/2016 | Hoover | A61K 33/14 |

FOREIGN PATENT DOCUMENTS

WO WO-2005065383 A2 * 7/2005 ........... A61K 9/0014

OTHER PUBLICATIONS

Pohl et al. Blood, Aug. 14, 2014, 124(7): 999-1009. (Year: 2014).*
Akong-Moore et al. PloS ONE, Aug. 2012, 7(8): e42984, pp. 1-7. (Year: 2012).*
Madan, Shilpi. "Check your salt." Published on Nov. 27, 2017. Retrieved online on Nov. 16, 2020. Retrieved from URL: <https://www.livemint.com/Leisure/yqxl5Iq4Gj2dCEJNLxS2xJ/Check-your-salt.html>, pp. 1-7. (Year: 2017).*
The Meadow. "Minerals in Himalayan Pink Salt: Spectral Analysis." Retrieved online on Nov. 16, 2020, Retrieved from URL: <https://themeadow.com/pages/minerals-in-himalayan-pink-salt-spectral-analysis>, pp. 1-5. (Year: 2020).*

* cited by examiner

*Primary Examiner* — Doan T Phan
(74) *Attorney, Agent, or Firm* — Knobbe, Martens, Olson & Bear LLP

(57) ABSTRACT

Disclosed herein are methods and compositions for treating, inhibiting, or ameliorating pulmonary infections, including cystic fibrosis. Aspects described herein relate to compositions including a saline solution and hypochlorite and methods of using these compositions alone or in combination with additional compounds, including antibiotics, an anti-inflammatories, bronchodilators, mucolytics, or oxygen therapy for treating, ameliorating, or inhibiting a pulmonary infection, including cystic fibrosis.

20 Claims, 18 Drawing Sheets

COMPOSITIONS AND METHODS FOR THE TREATMENT OF CYSTIC FIBROSIS

RELATED APPLICATIONS

This application claims the benefit of priority to U.S. Provisional Patent Application No. 62/662,325, filed on Apr. 25, 2018, the disclosure of which is incorporated by reference herein in its entirety.

FIELD

The present disclosure relates to methods and compositions for treating, inhibiting, or ameliorating a pulmonary infection in a subject, including cystic fibrosis, or symptoms of a pulmonary infection, including symptoms of cystic fibrosis. Specifically, the present disclosure is related to pharmaceutical compositions including a saline solution and hypochlorite for reducing the presence of an infectious organism in the lung, and methods of using the compositions for treating cystic fibrosis.

BACKGROUND

Airway secretions and their constituents play an important part in the defense of the respiratory tract. Respiratory secretions typically consist of a mixture of mucus, glandular products and plasma proteins and are produced by submucosal glands, goblet cells, and mucous cells located through the tracheobronchial system. Airway mucus secretion in general is poorly understood. Alder, K. L., Y. Li., *Am J Respir Cell Mol Bio,* 25:397-400 (2001).

Cystic fibrosis is a recessive genetic disease that manifests itself in multiple body systems, including, but not limited to chronic obstructive pulmonary disease (COPD)-like disease, pancreatic exocrine deficiency, urogenital dysfunction, and abnormally high electrolyte concentration in the sweat of the cystic fibrosis patient. Clinical manifestations may include nasal polyps, bronchiectasis, bronchitis, pneumonia, respiratory failure, gall bladder disease, intussusception, meconium ileus, salt depletion, pancreatic exocrine deficiency causing intestinal malabsorption of fats, proteins, and to a lesser extent, carbohydrates, pancreatitis, peptic ulcers, rectal prolapse, diabetes, nutritional deficiencies, arthritis, vas deferens with consequent aspermia and absence of fructose in the ejaculate, failure to thrive, and delayed puberty. The cystic fibrosis patient faces a high risk of morbidity and mortality due to frequent pulmonary infection.

SUMMARY

It is therefore an aspect of this disclosure to provide pharmaceutical compositions and methods of using the compositions for the treatment, prophylaxis, amelioration, or inhibition of pulmonary infections, including cystic fibrosis and for the treatment, prophylaxis, amelioration, or inhibition of symptoms of pulmonary infections, including cystic fibrosis.

Some embodiments provided herein relate to a method for treating a pulmonary infection in a subject. In some embodiments, the method includes administering to a subject a composition. In some embodiments, the composition includes 0.9% saline solution and 75 ppm hypochlorite. In some embodiments, the method further includes selecting a subject in need of treatment. In some embodiments, the pulmonary infection is cystic fibrosis. In some embodiments, the method further includes administering an antibiotic agent, an anti-inflammatory agent, a bronchodilator, a mucolytic agent, or oxygen therapy. In some embodiments, the composition is administered intranasally or by inhalation.

In some embodiments, the antibiotic agent is an aminoglycoside derivative like amikacin, gentamicin, kanamycin, neomycin, netilmicin, tobramycin, paromomycin; an ansamycin derivative like geldanamycin, herbimycin; a carbacephem derivative like loracarbef; a carbapenem derivative like ertapenem, doripenem, imipenem, meropenem; a cephalosporin derivative like cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole; a glycopeptide derivative like teicoplanin, vancomycin, telavancin; a lincosamides like clindamycin, lincomycin; a lipopeptide derivative like daptomycin; a macrolide derivative like azithromycin, clarithromycin, dirithromycin, erythromycin, roxithromycin, troleandomycin; telithreomycin, spectinomycin; a monobactam derivative like aztreonam; a nitrofuran derivative like furazolidone, nitrofurantoin; a penicillin derivative like amoxicillin, ampicillin, azlocillin, carbinicillin, cloxacillin, dicloxacillin, flucloxacillin, mezlocillin, methicillin, nafcillin, oxacillin, penicillin G, penicillin V, piperacillin, temocillin, ticarcillin; a penicillin combination like amoxicillin/clavulanate, ampicillin/sulbactam, piperacillin/tazobactam, ticarcillin/clavulanate; a polypeptide derivative like bacitracin, colistin, polymyxin B; a quinolone derivative like ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin; a sulfonamide derivative like mafenide, sulfonamidochrysoidine, sulfacetamide, sulfadiazine, silver sulfadiazine, sulfamethoxazole, sulfanilimide, sulfasalazine, sulfisoxazole, trimethoprim, trimethoprim/sulfamethoxazole; a tetracycline derivative like demeclocycline, doxycycline, minocycline, oxytetracycline, tetracycline; a derivative against mycobacteria like clofazimine, dapsone, capreomycin, cycloserine, ethambutol, ethioamide, isoniazid, pyrazinamide, rifampin, rifampicin, rifabutin, rifapentine, streptomycin; or arsphenamine, chloramphenicol, fosfomycin, fusidic acid, linezolid, metronidazole, mupirocin, platensimycin, quinupristin/dalfopristin, rifaximin, thiampheniol, tigecycline, amphotericins, novobiocins, polymixins, gramicidins, framycetin, ribostamycin, arbekacin, bekanamycin (kanamycin B), dibekacin, hygromycin B, sisomicin, isepamicin, verdamicin, astromicin, neamine, ribostamycin, lividomycin, or tinidazole or any salts or variants thereof.

In some embodiments, the anti-inflammatory agent is aspirin, diflunisal, salsalate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, nabumetone, diclofenac, piroxicam, meloxicam, tenoxicam, droxicam, lornoxicam, isoxicam, mefenamic acid, meclofenamic acid, flufenamic acid, tolfenamic acid, celecoxib, parecoxib, etoricoxib, lumiracoxib, fluticasone propionate/salmeterol (Advair® or Seretide®), montelukast (Singulair®), firocoxib, hydrocortisone, cortisone, prednisone, prednisolone, methylprednisolone, dexamethasone, betamethasone, triamcinolone, beclometasone, or fludrocortisone.

In some embodiments, the bronchodilator is albuterol, levalbuterol, pirbuterol, epinephrine, ephedrine, terbutaline, salmeterol, clenbuterol, formoterol, bambuterol, or indacaterol.

In some embodiments, the mucolytic agent is hypertonic saline, acetylcysteine, ambroxol, bromhexine, carbocisteine, domiodol, dornase alfa, eprazinone, erdosteine, letosteine, mannitol, mesna, mecysteine, neltenexine, sobrerol, stepronin, guaifenesin, guaiacolculfonate, ammonium chloride, potassium iodide, tyloxapol, antimony pentasulfide, guiaicol, iodinated glycerol, mensa, terpin, denufosol, bronchitol, or tiopronin.

In some embodiments, the method further includes administering ivacaftor, lumacaftor, tezacaftor, or analogues, derivatives, or combinations thereof.

In some embodiments, the method further includes reducing the presence of an infectious organism in the lung. In some embodiments, the infectious organism is *Pseudomonas aeruginosa* or *Burkholderia cepacia*. In some embodiments, the presence of an infectious organism reduces a dependency on or use of an antibiotic therapy. In some embodiments, the antibiotic therapy is erythromycin, tobramycin, or vancomycin.

In some embodiments, the method further includes reducing mucus viscosity. In some embodiments, reducing mucus viscosity clears mucus buildup. In some embodiments, the method further includes promoting oxidation of nucleic acid material and oxidation of trapped organic materials. In some embodiments, reducing mucus viscosity reduces a dependency on or use of a mucolytic agent. In some embodiments, the mucolytic agent is dornase alfa, denufosol, acetylcysteine, hypertonic saline, or ambroxol.

In some embodiments, the method further includes enhancing cystic fibrosis transmembrane conductance regulator (CFTR) function in a lung. In some embodiments, enhancing CFTR function maintains a surface liquid interface required for proper cilia function.

In some embodiments, the method further includes reducing lung inflammation. In some embodiments, reducing lung inflammation reduces the use of non-steroidal anti-inflammatory drugs (NSAIDs). In some embodiments, the method further includes generating nitric oxide in blood vessels. In some embodiments, generating nitric oxide stimulates endothelial nitric-oxide synthesis (NOS).

Some embodiments provided herein relate to a method of reducing the presence of infectious microorganisms trapped in mucus. In some embodiments, the method includes administering a composition including saline solution and hypochlorite. In some embodiments, the composition includes 0.9% saline solution and 75 ppm hypochlorite. In some embodiments, reducing the presence of infectious microorganisms reduces use or dependency on antibiotic therapy. In some embodiments, the composition is formulated for intranasal or pulmonary administration. In some embodiments, the composition is formulated for administration by an inhaler or nebulizer into the endobronchial or nasal cavity of infected patients to treat lung infections. In some embodiments, the lung infection is cystic fibrosis.

Some embodiments provided herein relate to a method of reducing viscosity of mucus in the mucus layer of the airways, lungs, bronchi, and trachea through oxidation of nucleic acid material and trapped organic materials. In some embodiments, the method includes administration of a composition including saline solution and hypochlorite. In some embodiments, the composition includes 0.9% saline solution and 75 ppm hypochlorite. In some embodiments, reducing the viscosity of mucus reduces the frequency or necessity for administration of mucolytic medications, such as hypertonic saline, dornase alfa, or acetylcysteine. In some embodiments, the composition is formulated for administration by an inhaler or nebulizer into the endobronchial or nasal cavity of infected patients to reduce mucus viscosity.

Some embodiments provided herein relate to a method of enhancing CFTR function in a lung. In some embodiments, the method includes administering a composition including saline solution and hypochlorite. In some embodiments, the composition includes 0.9% saline solution and 75 ppm hypochlorite. In some embodiments, the composition is formulated for administration by an inhaler or nebulizer into the endobronchial or nasal cavity of infected patients to enhance CFTR function. In some embodiments, enhancing CFTR function maintains the surface liquid interface required for proper cilia function. In some embodiments, the composition is administered in combination with albuterol or hypertonic saline.

Some embodiments provided herein relate to a method of reducing inflammation in a lung. In some embodiments, the method includes administering a composition including saline solution and hypochlorite. In some embodiments, the composition includes 0.9% saline solution and 75 ppm hypochlorite. In some embodiments, the composition is formulated for administration by an inhaler or nebulizer into the endobronchial or nasal cavity of infected patients to reduce inflammation. In some embodiments, reducing inflammation in the lung reduces use or dependency of anti-inflammatory agents, such as ibuprofen or other NSAIDs.

Some embodiments provided herein relate to a method of simulating endothelial nitric oxide synthesis. In some embodiments, the method includes administering a composition including saline solution and hypochlorite. In some embodiments, the composition includes 0.9% saline solution and 75 ppm hypochlorite. In some embodiments, the composition is formulated for administration by an inhaler or nebulizer into the endobronchial or nasal cavity of infected patients to stimulate endothelial nitric oxide synthesis. In some embodiments, stimulating endothelial nitric oxide synthesis generates nitric oxide in blood vessels that are involved in regulating vascular function.

Some embodiments provided herein relate to a method for treating a digestive dysfunction in a subject. In some embodiments, treating a digestive dysfunction in a subject includes administering to a subject a composition including 0.9% saline solution and 75 ppm hypochlorite. In some embodiments, the composition is administered orally. In some embodiments, the method further includes enhancing CFTR function in the gut. In some embodiments, enhancing CFTR function in the gut fosters digestive activity in the colon.

Some embodiments provided herein relate to a composition. In some embodiments, the composition includes 0.9% saline solution and 75 ppm hypochlorite. In some embodiments, the composition is formulated as a solution for oral administration. In some embodiments, the composition is formulated as a solution for intranasal administration. In some embodiments, the composition is formulated as an inhalable composition.

In some embodiments, the composition includes an active species. In some embodiments, the active species is ozone, active chlorine, active oxygen, or active hydrogen species. In some embodiments, the composition further includes ivacaftor, lumacaftor, tezacaftor, or analogues, derivatives, or combinations thereof.

In some embodiments, the composition further includes an antibiotic agent, an anti-inflammatory agent, a bronchodilator, a mucolytic agent, or oxygen therapy. In some embodiments, wherein the antibiotic agent is erythromycin, tobramycin, or vancomycin. In some embodiments, the antibiotic agent is an aminoglycoside derivative like amikacin, gentamicin, kanamycin, neomycin, netilmicin, tobramicin, paromomycin; an ansamycin derivative like geldanamycin, herbimycin; a carbacephem derivative like loracarbef; a carbapenem derivative like ertapenem, doripenem, imipenem, meropenem; a cephalosporin derivative like cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole; a glycopeptide derivative like teicoplanin, vancomycin, telavancin; a lincosamides like clindamycin, lincomycin; a lipopeptide derivative like daptomycin; a macrolide derivative like azithromycin, clarithromycin, dirithromycin, erythromycin, roxithromycin, troleandomycin; telithreomycin, spectinomycin; a monobactam derivative like aztreonam; a nitrofuran derivative like furazolidone, nitrofurantoin; a penicillin derivative like amoxicillin, ampicillin, azlocillin, carbinicillin, cloxacillin, dicloxacillin, flucloxacillin, mezlocillin, methicillin, nafcillin, oxacillin, penicillin G, penicillin V, piperacillin, temocillin, ticarcillin; a penicillin combination like amoxicillin/clavulanate, ampicillin/sulbactam, piperacillin/tazobactam, ticarcillin/clavulanate; a polypeptide derivative like bacitracin, colistin, polymyxin B; a quinolone derivative like ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin; a sulfonamide derivative like mafenide, sulfonamidochrysoidine, sulfacetamide, sulfadiazine, silver sulfadiazine, sulfamethoxazole, sulfanilimide, sulfasalazine, sulfisoxazole, trimethoprim, trimethoprim/sulfamethoxazole; a tetracycline derivative like demeclocycline, doxycycline, minocycline, oxytetracycline, tetracycline; a derivative against mycobacteria like clofazimine, dapsone, capreomycin, cycloserine, ethambutol, ethioamide, isoniazid, pyrazinamide, rifampin, refampicin, rifabutin, rifapentine, streptomycin; or arsphenamine, chloramphenicol, fosfomycin, fusidic acid, linezolid, metronidazole, mupirocin, platensimycin, quinupristin/dalfopristin, rifaximin, thiamphenol, tigecycline, amphotericins, novobiocins, polymixins, gramicidins, framycetin, ribostamycin, arbekacin, bekanamycin (kanamycin B), dibekacin, hygromycin B, sisomicin, isepamicin, verdamicin, astromicin, neamine, ribostamycin, lividomycin, or tinidazole or any salts or variants thereof.

In some embodiments, the anti-inflammatory agent is aspirin, diflunisal, salsalate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, nabumetone, diclofenac, piroxicam, meloxicam, tenoxicam, droxicam, lornoxicam, isoxicam, mefenamic acid, meclofenamic acid, flufenamic acid, tolfenamic acid, celecoxib, parecoxib, etoricoxib, lumiracoxib, fluticasone propionate/salmeterol (Advair® or Seretide®), montelukast (Singulair®), firocoxib, hydrocortisone, cortisone, prednisone, prednisolone, methylprednisolone, dexamethasone, betamethasone, triamcinolone, beclometasone, or fludrocortisone.

In some embodiments, the bronchodilator is albuterol, levalbuterol, pirbuterol, epinephrine, ephedrine, terbutaline, salmeterol, clenbuterol, formoterol, bambuterol, or indacaterol.

In some embodiments, the mucolytic agent is hypertonic saline, acetylcysteine, ambroxol, bromhexine, carbocisteine, domiodol, dornase alfa, eprazinone, erdosteine, letosteine, mannitol, mesna, mecysteine, neltenexine, sobrerol, stepronin, guaifenesin, guaiacolculfonate, ammonium chloride, potassium iodide, tyloxapol, antimony pentasulfide, guiaicol, iodinated glycerol, mensa, terpin, denufosol, bronchitol, or tiopronin.

BRIEF DESCRIPTION OF THE DRAWINGS

FIG. 2A depicts potential difference, FIG. 2B depicts basal current, and FIG. 2C depicts resistance. The bar graphs are shown in groups of four, with each group representing, from left to right: control, composition 1, composition 2, and composition 3.

FIG. 3A depicts results using DMSO and FIG. 3B depicts results using VS-809. The bar graphs are shown in groups of four, with each group representing, from left to right: control, composition 1, composition 2, and composition 3.

FIG. 4A depicts results using DMSO and FIG. 4B depicts results using VS-809. The bar graphs are shown in groups of four, with each group representing, from left to right: control, composition 1, composition 2, and composition 3.

FIG. 5A shows relative expression of TNFα mRNA, and FIG. 5B shows relative expression of IL-8 mRNA.

FIG. 6A shows relative expression of TNFα mRNA, and FIG. 6B shows relative expression of IL-8 mRNA.

FIG. 7A shows relative expression of TNFα mRNA, and FIG. 7B shows relative expression of IL-8 mRNA.

FIG. 8A shows relative expression of TNFα mRNA, and FIG. 8B shows relative expression of IL-8 mRNA.

FIG. 9A shows relative expression of TNFα mRNA, and FIG. 9B shows relative expression of IL-8 mRNA.

DETAILED DESCRIPTION

Figure 1:
FIG. 1 illustrates a schematic of embodiments of an experimental design for treatment of a cell culture using the compositions described herein.

Embodiments provided herein relate to methods and compositions for the treatment of pulmonary infections, including cystic fibrosis, in a subject in need. The methods of treating a pulmonary infection, including cystic fibrosis, includes administering to a subject or a patient having a pulmonary infection, such as cystic fibrosis, a therapeutically effective amount of a composition including a saline solution and hypochlorite, alone or in combination with an antibiotic to treat an infection of the lungs. Also provided are compositions that include a saline solution and hypochlorite, alone or in combination with an antibiotic.

It will be readily understood that the aspects of the present disclosure, as generally described herein, can be arranged, substituted, combined, separated, and designed in a wide variety of different configurations, all of which are explicitly contemplated herein.

Unless defined otherwise, technical and scientific terms used herein have the same meaning as commonly understood by one of ordinary skill in the art to which the present disclosure belongs. All patents, applications, published applications and other publications referenced herein are expressly incorporated by reference in their entireties unless stated otherwise. For purposes of the present disclosure, the following terms are defined below.

The articles "a" and "an" are used herein to refer to one or to more than one (for example, to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. When a value is preceded by the term about, the component is not intended to be limited strictly to that value, but it is intended to include amounts that vary from the value.

Throughout this specification, unless the context requires otherwise, the words "comprise," "comprises," and "comprising" will be understood to imply the inclusion of a stated step or element or group of steps or elements but not the exclusion of any other step or element or group of steps or elements.

As used herein, a "subject" or a "patient" refers to an animal that is the object of treatment, observation or experiment. "Animal" comprises cold- and warm-blooded vertebrates and invertebrates such as fish, shellfish, reptiles and, in particular, mammals. "Mammal" comprises, without limitation, mice, rats, rabbits, guinea pigs, dogs, cats, sheep, goats, cows, horses, primates, such as monkeys, chimpanzees, and apes, and, in particular, humans. In some alternatives, the subject is human.

Some embodiments disclosed herein relate to selecting a subject or patient in need. In some embodiments, a patient is selected who is in need of treatment, amelioration, inhibition, progression, or improvement in disease symptoms or who is in need of curative therapy. In some embodiments, a patient is selected who has symptoms of an infection of the lung, including symptoms of cystic fibrosis. In some embodiments, a patient is selected who has been diagnosed with a lung infection or who has been diagnosed with cystic fibrosis. Such identification or selection of said subjects or patients in need can be made through clinical and/or diagnostic evaluation. In some embodiments, a subject in need is a subject suffering from digestive dysfunction.

As used herein, the term "treatment" refers to an intervention made in response to a disease, disorder or physiological condition manifested by a subject, particularly a subject suffering from an infection of the lung, such as cystic fibrosis. The terms treating, treatment, therapeutic, or therapy do not necessarily mean total cure or abolition of the disease or condition. The aim of treatment may include, but is not limited to, one or more of the alleviation or prevention of symptoms, slowing or stopping the progression or worsening of the infection, curative treatment of the infection, or the remission of the infection. In some embodiments, treatment refers to both treatment of the underlying disease or treatment of the disease symptoms. For example, in some embodiments, treatments reduce, alleviate, ameliorate, or eradicate the symptom(s) of the disease and/or provide curative therapy of the disease.

The term "therapeutically effective amount" is used to indicate an amount of a composition that elicits the biological or medicinal response indicated. For example, a therapeutically effective amount of composition can be the amount needed to prevent, alleviate, or ameliorate symptoms of disease or prolong the survival of the subject being administered the therapy. This response may occur in a tissue, system, animal, or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As used herein, a "lung infection," "infection of the lung," or "pulmonary infection" refers to microbial pneumonias caused, for example, by viruses like Respiratory Syncytial Virus, Adenovirus, Herpes simplex, Influenza A, and others or bacteria like, *Pseudomonas aeruginosa, Staphylococcus aureus, Haemophilus influenzae, Klebsiella pneumoniae*, Group B *Streptococci, Enterobacter, Streptococcus pneumoniae, Burkholderia* species, such as *Burkholderia cepacia*, as well as fungi like *Aspergillus fumigatus, Pneumocystis carinii, Candida albicans*, and others. Pulmonary infection also refers to cases of reduced immunity for example the immunoparalytic phase occurring during sepsis and to immunodeficiency syndromes, whether congenital, spontaneously acquired, or iatrogenic. They are characterized by unusual susceptibility to infection and not infrequently to autoimmune disease and lymphoreticular malignancies. Patients with defects in humoral immunity have recurrent or chronic sinopulmonary infection, meningitis, and bacteremia, most commonly caused by pyogenic bacteria, such as *Haemophilus influenzae, Streptococcus pneumoniae*, and *Staphylococci*. These and other pyogenic organisms also cause frequent infections in individuals who have either neutropenia or a deficiency of the pivotal third component of complement (C3).

In some embodiments, an infection of the lung includes pulmonary inflammation. Inflammation of the lungs includes diseases like asthma, cystic fibrosis, or chronic obstructive pulmonary disease or conditions such as inflammation induced by allergens or acute respiratory distress syndrome.

As used herein, the term "cystic fibrosis (CF)" refers to an inherited disease characterized by an abnormality in the body's salt, water- and mucus-making cells. It is chronic, progressive, and is usually fatal, with no known cure. In general, children with CF live into their 30s. In addition to a complete medical history and physical examination, diagnostic procedures for cystic fibrosis may include the following: newborn screening; sweat (chloride) test to measure the amount of chloride in the sweat (higher than normal amounts of chloride may suggest cystic fibrosis); blood tests to determine mutations in the CFTR gene (other blood tests can assess infection, and involvement of certain organs);

chest x-rays; pulmonary function tests to measure the lungs' ability to exchange oxygen and carbon dioxide appropriately; sputum cultures to determine if an infection is present; stool evaluations to measure stool fat absorption; and pancreatic function tests.

Cystic fibrosis transmembrane conductance regulator (CFTR) protein is an ion channel protein that conducts chloride and thiocyanate ions across epithelia cell membranes. Mutations in CFTR lead to the dysregulation of epithelial fluid transport in the lung, pancreas, and other organs, and results in cystic fibrosis.

In addition, mutation in CFTR can result in digestive dysfunction. Some embodiments herein, therefore, relate to methods of treating a digestive dysfunction by enhancing CFTR function in the gut. As used herein, the term "digestive dysfunction" refers to a gastrointestinal disorder or condition, such as constipation, inflammatory bowel condition, indigestion, gastric reflux, bloating, gas, abdominal pain, diarrhea, heart-burn, irritable bowel syndrome, or a symptom associated with any of the aforementioned conditions. In some embodiments, the compositions described herein are formulated for oral administration, for example, as a drink, solution, or syrup, for enhancing CFTR function in the gut, thereby fostering digestive activity in the colon.

Some embodiments provided herein relate to compositions including a saline solution and hypochlorite. In some embodiments, the compositions herein are prepared or administered in a product combination e.g., the saline solution in combination with another therapeutic agent or therapy. Additional therapeutic agents and/or therapies that can be provided with the composition include for example, antibiotic therapy, anti-inflammatory therapy, bronchodilator therapy, mukinetic therapy, oxygen therapy, a cystic fibrosis therapy, or any combination thereof.

As used herein, the term "antibiotic therapy" refers to a treatment or amelioration of a disease or condition in which microbes are present. An antibiotic refers to any natural, synthetic, and semi-synthetic compound that will inhibit or reduce the growth of, or kill, one or more microorganisms, and has been identified as possessing antimicrobial activity, including, antibacterial, antifungal, antiviral, or antiparasitic activity. The antibiotic agent may be selected from aminoglycoside, ansamycin, carbacephem, carbapenem, cephalosporin, glycopeptide, lincosamide, lipopeptide, macrolide, monobactam, nitrofurans, penicillin, polypeptide, quinolone, sulfonamide, or tetracycline antibiotic. Examples of antibiotic agents include, but are not limited to, an aminoglycoside derivative like amikacin, gentamicin, kanamycin, neomycin, netilmicin, tobramicin, paromomycin; an ansamycin derivative like geldanamycin, herbimycin; a carbacephem derivative like loracarbef; a carbapenem derivative like ertapenem, doripenem, imipenem, meropenem; a cephalosporin derivative like cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole; a glycopeptide derivative like teicoplanin, vancomycin, telavancin; a lincosamides like clindamycin, lincomycin; a lipopeptide derivative like daptomycin; a macrolide derivative like azithromycin, clarithromycin, dirithromycin, erythromycin, roxithromycin, troleandomycin; telithreomycin, spectinomycin; a monobactam derivative like aztreonam; a nitrofuran derivative like furazolidone, nitrofurantoin; a penicillin derivative like amoxicillin, ampicillin, azlocillin, carbinicillin, cloxacillin, dicloxacillin, flucloxacillin, mezlocillin, methicillin, nafcillin, oxacillin, penicillin G, penicillin V, piperacillin, temocillin, ticarcillin; a penicillin combination like amoxicillin/clavulanate, ampicillin/sulbactam, piperacillin/tazobactam, ticarcillin/clavulanate; a polypeptide derivative like bacitracin, colistin, polymyxin B; a quinolone derivative like ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin; a sulfonamide derivative like mafenide, sulfonamidochrysoidine, sulfacetamide, sulfadiazine, silver sulfadiazine, sulfamethoxazole, sulfanilimide, sulfasalazine, sulfisoxazole, trimethoprim, trimethoprim/sulfamethoxazole; a tetracycline derivative like demeclocycline, doxycycline, minocycline, oxytetracycline, tetracycline; a derivative against mycobacteria like clofazimine, dapsone, capreomycin, cycloserine, ethambutol, ethioamide, isoniazid, pyrazinamide, rifampin, refampicin, rifabutin, rifapentine, streptomycin; or arsphenamine, chloramphenicol, fosfomycin, fusidic acid, linezolid, metronidazole, mupirocin, platensimycin, quinupristin/dalfopristin, rifaximin, thiampheniol, tigecycline, amphotericins, novobiocins, polymixins, gramicidins, framycetin, ribostamycin, arbekacin, bekanamycin (kanamycin B), dibekacin, hygromycin B, sisomicin, isepamicin, verdamicin, astromicin, neamine, ribostamycin, lividomycin, or tinidazole or any salts or variants thereof. In some embodiments, the antibiotic is useful in the treatment of cystic fibrosis. In some embodiments, the antibiotic agent is useful in the treatment of chronic obstructive pulmonary disease. The antibiotic used in combination with the compositions provided herein will depend on the type of infection.

As used herein "anti-inflammatory therapy" refers to a therapy that reduces inflammation. Anti-inflammatory agents include, but are not limited to, NSAIDS and glucocorticoids. Non-limiting examples of NSAIDS include aspirin, diflunisal, salsalate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, nabumetone, diclofenac, piroxicam, meloxicam, tenoxicam, droxicam, lornoxicam, isoxicam, mefenamic acid, meclofenamic acid, flufenamic acid, tolfenamic acid, celecoxib, parecoxib, etoricoxib, lumiracoxib, fluticasone propionate/salmeterol (Advair® or Seretide®), montelukast (Singulair®), and firocoxib. Glucocorticoids include, but are not limited to, hydrocortisone, cortisone, prednisone, prednisolone, methylprednisolone, dexamethasone, betamethasone, triamcinolone, beclometasone, or fludrocortisone.

As used herein, a "bronchodilator therapy" refers to a treatment that dilates the bronchi and bronchioles of the lung, and by doing so decrease resistance in the respiratory airway and increase airflow to the lungs. They are useful in bronchoconstrictive disorder such as asthma in which an obstruction of airflow and bronchospasm is involved. Examples of bronchodilator agents include, but are not limited to, β2-adrenergic receptor agonists such as albuterol, levalbuterol, pirbuterol, epinephrine, ephedrine, terbutaline, salmeterol, clenbuterol, formoterol, bambuterol, and indacaterol.

As used herein, a "mucokinetic therapy" refers to a treatment or agent that clears mucus present in the mucus layer of the airways, lungs, bronchi, and trachea. Mucokinetic agents include mucolytic agents, expectorants, and surfactants. Mucolytics are agents that dissolve thick mucus by dissolving various chemical bonds within secretions, which in turn can lower the viscosity by altering the mucin-containing components. Expectorants are agents that signal the body to increase the amount of hydration of secretions, resulting in clearer secretions. Surfactants act by wetting the mucus and allowing for mucus breakdown. Mucokinetic agents include, but are not limited to hypertonic saline, acetylcysteine ((2R)-2-acetamido-3-sulfanylpropanoic acid), ambroxol (trans-4-(2-Amino-3,5-dibrombenzylamino)-cyclohexanol), bromhexine (2,4-dibromo-6-{[cyclohexyl(methyl)amino]methyl}aniline), carbocisteine (R)-2-Amino-3-(carboxymethylsulfanyl)propanoic acid), domiodol ([2-(iodomethyl)-1,3-dioxolan-4-yl]methanol), dornase alfa (including recombinant human deoxyribonuclease I; also referred to as Pulmozyme®), eprazinone (3-[4-(2-ethoxy-2-phenyl-ethyl)piperazin-1-yl]-2-methyl-1-phenyl-propan-1-one), erdosteine (2-[(2-oxothiolan-3-yl)carbamoylmethylsulfanyl]acetic acid), letosteine (2-{2-[(2-ethoxy-2-oxoethyl)thio]ethyl}-1,3-4-carboxylic acid), mannitol, mesna (sodium 2-sulfanylethanesulfonate), mecysteine, neltenexine (N-(2,4-dibromo-6-{[(4-hydroxycyclohexyl)amino]methyl}phenyl)thiophene-2-carboxamide), and sobrerol ((1S)-5-(1-hydroxy-1-methylethyl)-2-methylcyclohex-2-en-1-ol), or stepronin (N-{2-[(2-thienylcarbonyl)thio]propanoyl}glycine), guaifenesin, guaiacolculfonate, ammonium chloride, potassium iodide, tyloxapol, antimony pentasulfide, guiaicol, iodinated glycerol, mensa, terpin, denufosol ([[(3S,5R)-5-(4-amino-2-oxopyrimidin-1-yl)-3-hydroxyoxolan-2-yl]lmethoxy-hydroxyphosphoryl][[(2R,3S,4R,5R)-5-(2,4-dioxopyrimidin-1-yl)-3,4-d ihydroxyoxolan-2-yl]methoxy-hydroxyphosphoryl]oxy-hydroxyphosphoryl]hydrogen phosphate), bronchitol, or tiopronin. Suitable mucokinetic agents are described more fully in the literature, such as in Goodman and Gilman, The Pharmacological Basis of Therapeutics (13th Edition), McGraw-Hill, 2014.

As used herein, a "cystic fibrosis" therapy includes any therapy that is used for the treatment of cystic fibrosis. Such therapies may include, for example, ivacaftor, lumacaftor, tezacaftor, or analogues, derivatives, or combinations thereof.

As used herein, the term "coadministration" of pharmacologically active compounds refers to the delivery of two or more separate chemical entities, whether in vitro or in vivo. Coadministration refers to the simultaneous delivery of separate agents; to the simultaneous delivery of a mixture of agents; as well as to the delivery of one agent followed by delivery of a second agent or additional agents. In all cases, agents that are coadministered are intended to work in conjunction with each other. Similarly, in the context of administration of more than one compound, the term "in combination" refers to a concomitant delivery of one compound with one or more compounds. The compounds may be administered in combination by simultaneous administration or administration of one compound before or after administration of another compound.

Cystic fibrosis is a recessive genetic disease that manifests itself in multiple body systems, including, but not limited to chronic obstructive pulmonary disease (COPD) like disease, pancreatic exocrine deficiency, urogenital dysfunction, and abnormally high electrolyte concentration in the sweat of the cystic fibrosis patient. Clinical manifestations may include nasal polyps, bronchiectasis, bronchitis, pneumonia, respiratory failure, gall bladder disease, intussusception, meconium ileus, salt depletion, pancreatic exocrine deficiency causing intestinal malabsorption of fats, proteins, and to a lesser extent, carbohydrates, pancreatitis, peptic ulcers, rectal prolapse, diabetes, nutritional deficiencies, arthritis, vas deferens with consequent aspermia and absence of fructose in the ejaculate, failure to thrive, and delayed puberty. The cystic fibrosis patient faces a high risk of morbidity and mortality due to frequent pulmonary infection.

Because cystic fibrosis is a genetically-determined illness, current treatments focus on treating, managing, alleviating, or ameliorating the symptoms of cystic fibrosis, with some qualifying patients receiving lung transplants. Current treatment standards, which may entail three to four hours of treatment per day for the patient, include one or more of the following treatment options.

1) Controlling the diet (high calorie/protein, high fat) in order to decrease the build-up of fats, proteins, and to a lesser extent, carbohydrates, which cannot be readily absorbed and metabolized. Typically, such dietary control is augmented with oral pancreatic enzymes to assist in fat metabolism.

2) Treating bacterial infections with erythromycin, tobramycin, and in severe infection cases, vancomycin to eradicate or control the infection (daily use of oral antibiotics may be prescribed as a preventive measure, due to the high frequency of lung infection, and its risk of mortality).

3) Treating mucosal buildup with mucolytic agents such as N-acetylcysteine and bronchodilator therapy with dornase alfa. Clinical response may further indicate bronchial drainage through recombinant human DNase (rhDNase), or flutter devices to assist in mucus airway clearance, together with clapping of the chest to dislodge mucus.

4) In extreme cases, bronchoalveolar lavage (BAL) to clear the lung. BAL refers to any medical procedure in which fluid (e.g., saline) is administered to a portion of a lung and is re-collected. Upon re-collection, BAL fluid samples may be analyzed, and may contain biological components including but not limited to cells (e.g., lung-resident mesenchymal stem cells, T-cells, bacterial cells, fungal cells) and non-cellular substances (e.g., cytokines, viruses, RNA, cellular protein, secreted protein, metabolites). Typically, a bronchoscope is used for administration and collection of BAL fluid. BAL procedures and the samples obtained thereby are not limited by the region of the lung to which fluid is administered, the type of fluid administered, the volume of fluid administered, or any other aspects of the procedure.

5) Periodic corticosteroid tablets and inhaled anti-asthma medications (e.g., Advair®, Singulair®, etc.) to combat lung inflammation (frequently resulting from the presence of infection), together with high doses of ibuprofen for its anti-inflammatory effect.

6) In addition, the cystic fibrosis patient may have insulin prescribed for cystic fibrosis-related diabetes, medications for cystic fibrosis-associated liver disease, and/or supplements of vitamins A and D together with medication to treat constipation.

7) Oxygen therapy (similar to that used with advanced COPD patients) may also be prescribed, which includes the inhalation of oxygen-enriched gas to compensate for the poor function of the patient's lungs in absorbing oxygen.

Symptom management therapies are moderately effective in controlling pulmonary infection with limited clearance of mucus. However, since even with the best available antibiotics such as tobramycin there may be as many as 45% of cystic fibrosis patients with drug-resistant infection. The presence of any bacterial pulmonary infection can prove life threatening. Further, should the more common bacterial infection be complicated by a simultaneous viral infection, the odds of mortality can increase for the infected cystic fibrosis patient. Lastly, since cystic fibrosis patient's build-up of mucus is genetically dependent, and the mucolytic agents and therapies are limited in total mucus-clearing effect (most only slow the progression of loss in pulmonary function, rather than improve pulmonary function on a statistically significant basis), the cystic fibrosis patient lives with a serious threat of respiratory failure with any of the frequent pulmonary infections. This risk tends to be compounded with the increasing age of the cystic fibrosis patient. Even with the use of all such therapies administered through approved cystic fibrosis disease centers, the common prognosis for life expectancy is currently age 31-32 (2002 data, Cystic Fibrosis Foundation).

New antimicrobial therapies that also effect an enhanced reduction of the continued mucus build-up are a desirable addition to the current armament against airway obstruction and frequent pulmonary infection. Should such therapies also prove less susceptible to drug resistance, together with efficacy on viruses, their value in extending the quality of life and life span of cystic fibrosis patients would be substantial.

The present disclosure relates to compositions including saline solution and hypochlorite. The compositions described herein may be used alone or in combination with antibiotic therapy, anti-inflammatory therapy, bronchodilator therapy, mucokinetic therapy, oxygen therapy, or any combination thereof. As will be readily apparent, the compositions described herein have a dual mechanism of action by both acting as an antimicrobial agent and also as a mucolytic agent. Thus, the compositions described herein provide promise for patients with cystic fibrosis by serving as a highly effective antimicrobial agent for pulmonary infections, with little or no probability of drug resistance and serving as best-of-breed mucolytic agent in clearing the continuous mucus build-up in cystic fibrosis, when administered into the lungs.

In some embodiments, the composition described herein includes a saline solution and a hypochlorite. As used herein, "saline solution" is a solution that includes a salt in an amount of 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, 4.5%, 5%, 6%, 7%, 8%, 9%, or 10%, or an amount within a range defined by any two of the aforementioned values. In some embodiments, the saline solution is prepared from a sterile saline solution.

In some embodiments, the salt used for the saline solution is unrefined, refined, caked, de-caked, or the like. In some embodiments, the salt is halite, table salt, common salt, curing salt, flake salt, Epsom salt, sea salt, Alaea salt (or Hawaiian sea salt), Alpenbergkern salt, Anglesey Sea salt, Celtic sea salt, Dead Sea salt, Himalayan sea salt (including Himalayan pink sea salt), Kalahari salt, Maras salt, Murray River salt flakes, Namibian salt pearls, Persian blue fine salt, Polish mine salt, primordial sea salts, Sal de Tavira, Sale Marino di Trapani, Sel de Guérande, South African Sea salt, Utah salt, black lava salt, brine, rock salt, red rock salt, fleur de sel, or kosher salt. The salt present in the saline solution can include a number of elements, including, for example, actinium, aluminum, antimony, arsenic, astatine, barium, beryllium, bismuth, boron, bromine, cadmium, calcium, carbon, cerium, cesium, chlorine, chromium, cobalt, copper, dysprosium, erbium, europium, francium, fluorine, gadolinium, gallium, germanium, gold, hafnium, holmium, hydrogen, iodine, indium, iridium, iron, lanthanum, lead, lithium, lutetium, magnesium, manganese, mercury, molybdenum, neptunium, neodymium, nickel, niobium, nitrogen, osmium, oxygen, palladium, phosphorus, platinum, plutonium, polonium, potassium, praseodymium, promethium, protactinium, radium, rhenium, rhodium, rubidium, ruthenium, samarium, scandium, selenium, silicon, silver, sodium, strontium, sulfur, tantalum, technetium, tellurium, terbium, thallium, thorium, thulium, tin, titanium, uranium, vanadium, ytterbium, zinc, or zirconium. In some embodiments, the element present in the salt can be present in an amount of less than 0.001 ppm to an amount of greater than 400,000 ppm.

In some embodiments, the saline solution may include a salt that includes aluminum in an amount of 114.8 ppm, antimony in an amount of 0.022 ppm, arsenic in an amount of 0.066 ppm, barium in an amount of 0.664 ppm, beryllium in an amount of 0.051 ppm, bismuth in an amount of 0.005 ppm, bromine in an amount of 56.006 ppm, cadmium in an amount of 0.017 ppm, calcium in an amount of 2101 ppm, chromium in an amount of 0.207 ppm, cobalt in an amount of 0.033 ppm, copper in an amount of 0.116 ppm, germanium in an amount of 0.072 ppm, iodide in an amount of less than 0.001 ppm, iron in an amount of 81.722 ppm, lead in an amount of 0.093 ppm, magnesium in an amount of 1944 ppm, manganese in an amount of 1.911 ppm, mercury in an amount of 0.016 ppm, molybdenum in an amount of 0.011 ppm, nickel in an amount of 0.096 ppm, phosphorus in an amount of 5.125 ppm, potassium in an amount of 1728 ppm, selenium in an amount of 0.269 ppm, silver in an amount of 0.004 ppm, sodium in an amount of 388690 ppm, strontium in an amount of 32.223 ppm, tin in an amount of 0.169 ppm, or zinc in an amount of 1.261 ppm or any combination thereof. In some embodiments, the saline solution includes one or more of the above elements present in 1, 2, 3, 4, 5, 6, 7, 8, 9, or 10% higher or lower than the above-listed amounts.

In some embodiments, the saline solution may include a salt that includes aluminum in an amount of 0.747 ppm, antimony in an amount of 0.014 ppm, arsenic in an amount of 0.039 ppm, barium in an amount of 0.012 ppm, beryllium in an amount of 0.038 ppm, bismuth in an amount of 0.005 ppm, bromine in an amount of 81.414 ppm, cadmium in an amount of 0.007 ppm, calcium in an amount of 10.625 ppm, chromium in an amount of 0.027 ppm, cobalt in an amount of 0.001 ppm, copper in an amount of 0.053 ppm, germanium in an amount of 0.081 ppm, iodide in an amount of less than 0.001 ppm, iron in an amount of 0.639 ppm, lead in an amount of 25.908 ppm, magnesium in an amount of 3.753 ppm, manganese in an amount of 0.040 ppm, mercury in an amount of 0.013 ppm, molybdenum in an amount of 0.007 ppm, nickel in an amount of 0.016 ppm, phosphorus in an amount of 3.690 ppm, potassium in an amount of 60.756 ppm, selenium in an amount of 0.202 ppm, silver in an amount of 0.002 ppm, sodium in an amount of 391290 ppm, strontium in an amount of 0.230 ppm, tin in an amount of 0.166 ppm, or zinc in an amount of 0.791 ppm or any combination thereof. In some embodiments, the saline solution includes one or more of the above elements present in 1, 2, 3, 4, 5, 6, 7, 8, 9, or 10% higher or lower than the above-listed amounts.

In one embodiment, the salt is sodium chloride (NaCl), lithium chloride (LiCl), hydrogen chloride (HCl), copper chloride ($CuCl_2$), copper sulfate ($CuSO_4$), potassium chloride (KCl), magnesium chloride (MgCl), calcium chloride ($CaCl_2$), or sulfates or phosphates. In some embodiments, the salt can include an additive. Salt additives can include, but are not limited to potassium iodide, sodium iodide, sodium iodate, dextrose, sodium fluoride, sodium ferrocyanide, tricalcium phosphate, calcium carbonate, magnesium carbonate, fatty acids, magnesium oxide, silicon dioxide, calcium silicate, sodium aluminosilicate, calcium aluminosilicate, ferrous fumarate, iron, or folic acid. Any of these additives can be added at this point or at any point during the described process. For example, the above additives can be added just prior to packaging the composition.

In some embodiments, the saline solution is electrolyzed to produce an amount of active species, including ozone, active chlorine, active oxygen, or active hydrogen species. In some embodiments, the ozone is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, 100, 150, 200, 250, or 300 ppm or an amount within a range defined by any two of the aforementioned values. In some embodiments, the active chorine species is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, 100, 150, 200, 250, or 300 ppm or an amount within a range defined by any two of the aforementioned values. In some embodiments, the active chorine species is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, 100, 150, 200, 250, or 300 ppm or an amount within a range defined by any two of the aforementioned values. In some embodiments, the active oxygen species is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, 100, 150, 200, 250, or 300 ppm or an amount within a range defined by any two of the aforementioned values. In some embodiments, the active hydrogen species is present in an amount of 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, 100, 150, 200, 250, or 300 ppm or an amount within a range defined by any two of the aforementioned values. The process of electrolysis may be performed using any suitable voltage, current, time, or conditions to prepare the saline solution according to the desired concentration of active species.

"Hypochlorous acid" or "hypochlorite" as used herein, refers to a weak acid having the chemical formula HClO. Hypochlorous acid is also known as chloric (I) acid, chloranol, or hydroxidochlorine. Salts of hypochlorite are also referred to herein and can include sodium hypochlorite (NaClO), calcium hypochlorite ($Ca(ClO)_2$), or potassium hypochlorite (KClO). As described herein, hypochlorous acid and hypochlorite are used as killing agents, cleansing agents, disinfectants, bleaching agents, whitening agents, antibacterial agents, sanitizers, and/or preservatives. Hypochlorite, or acids and salts thereof, may be used in the compositions of the present disclosure at an amount of about 0.5%, 1%, 5%, 10%, 15%, 20%, 25%, 30%, 40%, 50%, or greater w/v %, or within a range defined by any two of the aforementioned amounts. In some embodiments, the w/v % of hypochlorite or an acid or salt thereof is about 25% w/v. In some embodiments, the hypochlorite salt or hypochlorous acid is added directly to the composition. In some embodiments, the final amount of hypochlorous acid is less than, greater than, or equal to about 10, 15, 20, 25, 30, 35, 40, 45, 50, 55, 60, 65, 70, 75, 80, 85, 90, 95, 100, 120, 150, 175, 200, 300 ppm or within a range defined by any two of the aforementioned amounts. In some embodiments, the amount of hypochlorous acid in the composition is between about 50 to about 100 ppm. In some embodiments, the amount of hypochlorous acid in the composition is about 75 ppm.

In some embodiments, the compositions described herein include saline solution and hypochlorite, and further include a therapy for treating cystic fibrosis, including an antibiotic, an anti-inflammatory, a bronchodilator, a mucokinetic, oxygen therapy, or any combination thereof. Thus, a lung infection, including cystic fibrosis, may be treated with existing treatments for lung infections, such as cystic fibrosis, such as antibiotic therapy, anti-inflammatory therapy, bronchodilator therapy, mucokinetic therapy, oxygen therapy, or any combination thereof in addition or in combination with the composition including a saline solution and hypochlorite. In some embodiments, a subject suffering from a lung infection, such as from cystic fibrosis, is provided one or more of the aforementioned treatments before, after, or simultaneous with administration of a saline composition and hypochlorite.

In some embodiments, the compositions provided herein further include a pharmaceutically acceptable carrier. In some embodiments, the pharmaceutically acceptable carrier facilitates administration and uptake of the composition into cells or tissues. In some embodiments, the pharmaceutically acceptable carrier may include excipients, suspending agents, diluents, fillers, salts, buffers, stabilizers, solubilizers, solvents, dispersion media, coatings, isotonic agents, and other materials known in the art. The pharmaceutical formulation optionally includes potentiators, complexing agents, targeting agents, stabilizing agents, cosolvents, pressurized gases, or solubilizing conjugates.

In some embodiments, excipients include sugars such as lactose, sucrose, mannitol, or sorbitol; cellulose preparations such as, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP).

In some embodiments, suspending agents include oleic acid, simple carboxylic acid derivatives, and sorbitan trioleate. In some embodiments, diluents include water, saline, phosphate-buffered citrate, mucolytic preparations, alcohol, propylene glycol, and ethanol; these solvents or diluents are more common in oral aerosol formulations. Physiologically acceptable diluents that have a tonicity and pH compatible with the alveolar apparatus are desirable.

In some embodiments, fillers include glycerin, propylene glycol, ethanol in liquid or fluid preparations. Suitable fillers for dry powder inhalation systems include lactose, sucrose, dextrose, suitable amino acids, and derivatives of lactose. In some embodiments, salts include those that are physiologically compatible and provide the desired tonicity adjustment. Monovalent and divalent salts of strong or weak acids are desirable. In some embodiments, buffers include phosphate or citrate buffers or mixed buffer systems of low buffering capacity.

In some embodiments, stabilizers include those that provide chemical or physical stability of the final preparations. Such stabilizers include antioxidants such a sodium metabisulfite, alcohol, polyethylene glycols, butylated hydroxyanisole, butylated hydroxytoluene, disodium edetate. Included within this class of stabilizers are cryoprotectants such as polyethylene glycols, sugars, and carrageenans.

In some embodiments, solubilizers include propylene glycol, glycerin, suitable amino acids, complexing agents such as cyclodextrins, sorbitol solution, or alcohol. Solubilizers including ethanol, propylene glycol, glycerin, sorbitol, and cyclodextrins are desirable.

The amount of the pharmaceutically acceptable excipient may vary from or any number in between 1% to about 75% by weight of the total pharmaceutical composition. In some embodiments, the amount of excipient ranges from or any number in between 1-5%, 2-7%, 5-10%, 7-12%, 10-15%, 12-17%, 15%-20%, 17%-22%, 20%-25%, 22%-27%, 25%-30%, 27%-32%, 30%-35%, 32%-37%, 35%-40%, 37%-

42%, 40%-45%, 40-50%, 45-55%, 50-60%, 55-65%, 60-70%, or 65-75% by weight of the total pharmaceutical composition or within a range defined by any two of the aforementioned amounts. In some embodiments, the amount of excipient is at least 5%, at least 10%, at least 15%, at least 20%, at least 25%, at least 30%, at least 40%, at least 50%, at least 60%, at least 70%, or at least 75% of the weight of the total pharmaceutical composition or within a range defined by any two of the aforementioned amounts. In some embodiments, the amount of excipient is less than 5% of the weight of the total pharmaceutical composition.

As used herein, the term "surfactant" refers to a surface active compound. A surface active compound is a compound or substance that lowers the surface tension of a material containing the substance by adsorption on the interface. A surfactant can be a pure chemical compound or a mixture of different chemical compounds. Surfactants can include lecithin, monoglycerides, monostearates, ethoxylates, sulfates, and sulfates of ethoxylates such as sodium dodecyl sulfate (SDS or sodium lauryl sulfate), sodium laureth sulfate (SLES), sodium coco sulfate (SCS). The surfactant may be used in the composition in an amount of about 0.1%, 0.25%, 0.5%, 0.75%, 1%, 1.5%, 2%, 2.5%, 3%, 3.5%, 4%, 4.5%, 5%, 6%, 7%, 10%, 15%, or greater w/v %, or in an amount within any two of the aforementioned values or between a range defined by these values. In some embodiments, the amount of surfactant is about 1% w/v.

As used herein, the term "buffer" refers to solutions that resist changes in pH by the action of its conjugate acid-base range. The buffer may be used as an initial solution in the manufacture of the composition, and then modified for the specified use, such as for formulation of a composition for the particular mode of administration, whether oral, intranasal, or pulmonary. Examples of buffers can include citrate, phosphate, acetate, or other mineral acid or organic acid buffers, or combinations thereof. In some embodiments, the buffer is a phosphate buffer, such as sodium phosphate monobasic, potassium phosphate dibasic, tri potassium phosphate, or other salts of phosphate. As described herein, the buffer may be used for adjustment of pH, as a thickening agent by the introduction of ions, or as a buffer. The buffer may be used in the composition in an amount of about 0.05%, 0.1%, 0.2%, 0.3%, 0.4%, 0.5%, 1%, 1.5%, 2%, 2.5%, 3%, 3.5%, 4%, 4.5%, 5%, 6%, 7%, 10%, 15%, or greater w/v %, or in an amount within any two of the aforementioned values.

As used herein, the pH of the composition is the numerical scale to specify the acidity or basicity of the formulation. In some embodiments, the pH of the formulation is about 5.0, 5.5, 6.0, 6.5, 6.6, 6.7, 6.8, 6.9, 7.0, 7.1, 7.2, 7.3, 7.4, 7.5, 7.6, 7.7, 7.8, 7.9, 8.0, or 8.5, or within a ranged defined by any two of the aforementioned values. In some embodiments, the pH of the composition is in a range from about 6.5 to about 7.5.

The compositions described herein may further include an additive known in the art. Exemplary additives include sweeteners, preservatives, emulsifiers, detergents, emollients, moisturizers, humectants, pigments, dyes, pearlescent compounds, effervescent agents, calcium, fluoride, titanium dioxide coated mica, colorants, fragrances, flavorants, biocides, alpha hydroxy acids, antioxidants, anti-microbial agents, anti-fungal agents, exfoliants, hormones, enzymes, medicinal compounds, vitamins, salts, electrolytes, alcohols, polyols, polypropylene glycol, polyisobutene, polyoxyethylene, behenic acid, behenyl, sugar-alcohols, botanical extracts, surfactants, organic oils, waxes, alkaline or acidic or buffering agents, film formers, thickening agents, hyaluronic acid, fumed silica, talc, kaolin, starch, modified starch, mica, nylon, clay, bentonite, organo-modified clays, and combinations thereof.

The compositions of the disclosure may be prepared, packaged, or sold in formulations suitable for oral, topical, pulmonary, intranasal, or another route of administration. The compounds may be administered by any convenient route, for example by absorption through epithelial or mucocutaneous linings (e.g., oral mucosa or intestinal mucosa), and may be administered together with other agents as described herein. Further, administration may be by a single dose or a series of doses.

In some embodiments, the compositions provided herein are formulated for nasal administration. Thus, a formulation for nasal administration may be provided as a nasal spray or as nasal drops.

In some embodiments, the compositions are formulated for inhalation. An inhalation formulation can be used to achieve high local concentrations. Formulations suitable for inhalation include dry power or aerosolized or vaporized solutions, dispersions, or suspensions capable of being dispensed by an inhaler or nebulizer into the endobronchial or nasal cavity of infected patients to treat lung infections, such as cystic fibrosis.

In some embodiments, the composition is formulated for oral administration. In some embodiments, the oral formulation is provided as a solution, suspension, syrup, or elixir. In some embodiments, an oral formulation is provided as a drink to enhance CFTR function in the gut to foster digestive activity within the colon.

Compositions for oral, topical, pulmonary, or intranasal administration may be obtained by combining a composition including a saline solution and hypochlorite, alone or in combination with one or more of an antibiotic, an anti-inflammatory, a bronchodilator, a mucokinetic, or oxygen therapy, with one or more pharmaceutically acceptable carriers and/or excipients, and formulation the composition for the specific mode of administration, whether oral, nasal, or by inhalation. The compositions including a saline solution and hypochlorite, alone or in combination with one or more of an antibiotic, an anti-inflammatory, a bronchodilator, a mucokinetic, or oxygen therapy, may be manufactured by mixing, dissolving, granulating, dragee-making, levigating, emulsifying, encapsulating, entrapping, or tabletting processes.

The composition may be presented in a bottle, package, nebulizer, inhaler, or dispenser device, which may contain one or more unit dosage forms containing a saline solution and hypochlorite composition, alone or in combination with one or more of antibiotic, an anti-inflammatory, a bronchodilator, a mucokinetic, or oxygen therapy. The bottle, package, nebulizer, inhaler, or dispenser device may be accompanied by instructions for administration. The bottle, package, nebulizer, inhaler, or dispenser device may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. The composition including a saline solution and hypochlorite, alone or in combination with one or more of an antibiotic, an anti-inflammatory, a bronchodilator, a mucokinetic, or oxygen therapy, may be placed in an appropriate container, and labeled for treatment of an indicated condition, such as for treatment of a lung infection, such as cystic fibrosis.

In some embodiments, the compositions including the saline solution and hypochlorite, alone or in combination with one or more of an antibiotic, an anti-inflammatory, a bronchodilator, a mucokinetic, or oxygen therapy, can be stable for at least 1 week, 2 weeks, 3 weeks, 1 month, 2 months, 3 months, 6 months, 9 months, 12 months, 15 months, 18 months, 24 months, 36 months, or 48 months or within a range defined by any two of the aforementioned times.

In some embodiments, an intranasal dosage or dosage for oral inhalation of the electrolyzed saline solution may be between 0.01 mL/kg body weight/day to 10 mL/kg body weight/day. In some embodiments, the inhaled or intranasal dosage of the electrolyzed saline solution is between 0.25 to 4 mL/kg body weight/day, such as, e.g., from about 0.5 to 3.0 mL/kg body weight/day, such as, e.g., from about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3-0.1, about 3.2, about 3.3, about 3.4, about 3.5, about 3.6, about 3.7, about 3.8, about 3.9, or about 4.0 mL/kg body weight/day, or an amount within a range defined by any two of the aforementioned values.

The doses can be divided into smaller doses and administered two or more times per day or may be administered in a single dose. The regimen can vary according to the indication being treated. For example, it may be advantageous to administer the composition for several days followed by a rest period and repeating the cycle for as long as necessary or as indicated by test results. In some embodiments, the compositions may be administered when needed. In some embodiments, the composition may be administered twice daily for a period of 1 week, 2 weeks, 3 weeks, 1 month, 2 months, 3 months, 6 months, 9 months, 12 months, 15 months, 18 months, 24 months, 36 months, 48 months, 5 years, 6, years, 7, years, 8 years, 9 years, 10 years, 15 years, 20 years, 30 years, 40 years, or greater or within a range defined by any two of the aforementioned times. Depending on clinical status or laboratory tests, the amount and frequency of administration may be reduced.

Some embodiments disclosed herein relate to compositions including the saline solution and hypochlorite, alone or in combination with one or more of an antibiotic, an anti-inflammatory, a bronchodilator, a mucokinetic, or oxygen therapy, and methods of using such compositions to treat, inhibit, or ameliorate a lung infection, such as cystic fibrosis in a subject in need thereof.

The compositions provided herein have significant antimicrobial properties. Without wishing to be bound by theory, it is contemplated that the primary mechanism of action of the composition is due to the presence of reactive oxygen molecules, such as hypochlorite, present in the composition, which is capable of killing microbes, such as bacteria, trapped in the lungs either by direct contact or by boosting the innate immune system's ability to generate reactive oxygen species to the kill the pathogens.

Furthermore, because of the non-specific oxidation mediated killing mechanism of reactive oxygen species delivered in solution, there is a low probability that microbes, such as bacteria or viruses, can develop a resistance to the composition. The mechanism of action is a direct cellular interaction of the composition with the pathogen (when at sufficient concentration in vivo, effecting a direct pathogen-killing effect) through reactive oxygen species in the solution, acting in the same manner as polymorphonuclear neutrophils, macrophages, and eosinophils in their pathogen-killing effect. At lower concentrations in vivo, the compositions immobilize the pathogens. For pathogens immobilized but not killed by the compositions, they then become targets for normal pathogen-killing by neutrophilic, eosinophilic, and macrophagic myeloperoxide action. Because of this mechanism of action in killing pathogens, the emergence of drug-resistant pathogens is expected to be minimal, since the killing mechanism co-opts the pathogens' ability to mutate into survivable form.

The compositions provided herein exhibit exemplary pathogen-killing effect against various bacteria, including *P. aeruginosa* or *B. cepacia*, viruses, and fungi, both in vitro and in vivo. The compositions provided herein exhibited no drug resistance with such pathogens, nor systemic toxicity. Because many cystic fibrosis patients have chronic bacterial infection (typically *P. aeruginosa*, with up to 45% having drug-resistant strains), from which they eventually die (pneumonia or pulmonary sepsis), the use of a safe therapeutic that eradicates their chronic pulmonary infection could prove of great value. To do so without drug resistance or toxicity represents a significant improvement potential for added lifespan for patients with cystic fibrosis.

In addition, the compositions provided herein have significant mucolytic properties, as demonstrated in both its asthma and cystic fibrosis-like murine models (up to 100% mucus plug removed in 90% of treated mice). If the mucus deposition in cystic fibrosis patient lungs is managed through nebulization compliance several times per day, this also reduces the possibility of re-establishment of new bacterial or viral cultures in the patient's pulmonary mucus bed. The pulmonary function in cystic fibrosis patients using the compositions clinically improves on a statistically meaningful basis, a result of such effective mucolytic action. The anti-infective putative mucolytic mechanism of the composition includes oxidation of excess mucus production when administered by inhalation, for example through a nebulizer into the lungs. In addition, the composition turns mucus into small particulate form, enabling removal by white blood cells or through coughing and expectoration. Cystic fibrosis patients struggle with mucus clearance because of reduced surface liquid present at the interface of the cell membrane and cilia. The compositions provided herein exhibits mucusclearing action in mice when applied intra-nasally. The ability to continually remove the excess mucus build-up in cystic fibrosis patient lungs represents a first therapeutic to potentially improve pulmonary function to a significant, measurable degree. Further, by continually removing the accumulation of excess mucus deposition in the lungs' airways with daily nebulization, the mucus vehicle that proves as the attractant for pulmonary infection via various microbes, such as bacteria or viruses, is greatly reduced, thereby offering improved conditions for eliminating the chronic pulmonary infection with the compositions provided herein.

The composition including a saline solution and hypochlorite also stimulate endothelial nitric-oxide synthesis (NOS) by generating nitric oxide in blood vessels that are involved in regulating vascular function, thereby improving bronchial control.

Thus, together with the antimicrobial and mucolytic properties, the compositions provided herein can serve as an agent, alone or in combination with a treatment for a lung infection (such as an antibiotic, an anti-inflammatory, a bronchodilator, a mucokinetic, or oxygen therapy) in clearing the continuous mucus build-up when applied by nebulization into the lungs.

Accordingly, the compositions provided herein may be administered to treat a pulmonary infection, including pneumonia, cystic fibrosis, chronic obstructive pulmonary disease, bronchitis, asthma, or other lung disorders that may be associated with a pulmonary infection in a subject in need thereof. In some embodiments, the composition reduces the presence of an infectious organism due to the antimicrobial properties of the composition, or due to the stimulation of the innate immune system's ability to generate reactive oxygen species. In some embodiments, the infectious organism is *Pseudomonas aeruginosa* or *Burkholderia* species, such as *Burkholderia cepacia*. In some embodiments, reducing the presence of an infectious organism reduces the subject dependency on or use of antibiotic therapies. Because the infectious organism is reduced, the subject no longer requires the use of the antibiotic therapies to the same extent as prior to administration of the composition. In some embodiments, the antibiotic therapy includes erythromycin, tobramycin, or vancomycin.

In some embodiments, treatment with the composition including saline solution and hypochlorite reduces the presence or viscosity of mucus present in the mucus layer of the airways, lungs, bronchi, and trachea. Mucus present in the mucus layer of the airways, lungs, bronchi, and trachea include nucleic acids that generally come from at least two sources. One source of nucleic acid is microbial nucleic acids released as a function of immune cell mediate killing. A second source of nucleic acid is from lysis of exhausted neutrophil or eosinophil responding cells in the lungs. The cystic fibrosis lung is in an inflammatory state where immune response cells are responding to pathogens and also caught in a circular response pattern. Organic materials present are trapped in the mucus of the cystic fibrosis lung, and remain stuck in the lung because of the inability of the cilia to beat, and thereby clear the materials. The organic materials are the lytic debris of microbial pathogens and also the exhausted neutrophils or eosinophils that are present. Organic material in the lung can refer to trapped particulates in the lung unrelated to cell killing. The purpose of cilia and mucus is to trap airborne particulates in the mucus and sweep up the trapped particulates up the respiratory escalator for coughing up. In some embodiments, administration of the composition clears mucus buildup. In some embodiments, administration of the compositions described herein induce oxidation of the nucleic acid material. In some embodiments, administration of the compositions induce oxidation of organic material through reactive oxygen species chemistry. Because the presence of mucus is decreased or eliminated through administration of the compositions, the use of mucolytic compositions is decreased. Thus, in some embodiments, a subject that is treated with the compositions provided herein has reduced mucus viscosity or reduced mucus buildup, and therefore the use or necessity of a mucolytic is reduced.

In some embodiments, administration of the composition enhances cystic fibrosis transmembrane conductance regulator (CFTR) function in the lung. CFTR conducts chloride and thiocyanate ions across epithelia cell membranes. Enhanced function of the CFTR results in improved transmembrane flow of ions maintains a surface liquid interface, and results in a proper functioning of cilia present in the mucus layer.

In some embodiments, administration of the composition reduces lung inflammation. In pulmonary infections, including cystic fibrosis, inflammation is abnormally regulated. Increased neutrophils present in the airway result in persistent inflammation. Furthermore, the increased viscosity and presence of mucus further exacerbates inflammatory pathways. The compositions reduce mucus viscosity, reduce mucus buildup, and reduce microbial infections, thereby reducing inflammatory pathways. As a result, in some embodiments, administration of the composition results in decreased inflammation, and decreased dependence or use of anti-inflammatory medications.

EXAMPLES

Some aspects of the embodiments discussed above are disclosed in further detail in the following examples, which are not in any way intended to limit the scope of the present disclosure. Those in the art will appreciate that many other embodiments also fall within the scope of the invention, as it is described herein above and in the claims.

Example 1

Preparation of Lung Infection Compositions

The following example demonstrates a method of preparing a composition for use in treating a pulmonary infection.

A saline solution is sterilized and subjected to electrolysis. The saline solution includes 0.9% salt, and is electrolyzed under conditions sufficient to produce 75 ppm hypochlorite. Additional reactive oxygen species may be present in the solution along with hypochlorite.

The composition is useful for treatment of a pulmonary infection, and may be used alone or in combination with existing treatments of pulmonary infections, including with an antibiotic, an anti-inflammatory, a bronchodilator therapy, a mucokinetic therapy, oxygen therapy, or any combination thereof. In some embodiments, the composition is formulated as a composition for oral, intranasal, or pulmonary administration. For oral administration, the composition is formulated as a solution or drink. For intranasal administration, the composition is formulated as a nasal drop or nasal spray. For pulmonary administration, the composition is formulated for nebulization for inhalation into the lungs.

Example 2

Treatment of Bronchial Epithelial Cell Cultures

The following example demonstrates a method of treating a cell culture using the compositions described herein.

Cell Culture

F508del/F508del human bronchial epithelial cells (KK013K p2) were thawed and expanded on Pure-Col coated P100 tissue culture dishes in bronchial epithelial cell grown medium (BEGM). F508del is a specific mutation within the gene for the cystic fibrosis transmembrane conductance regulator (CFTR). The mutation is a deletion of three nucleotides spanning positions 507 and 508 of the CFTR gene on chromosome 7, which ultimately results in the loss of a single codon for the amino acid phenylalanine (F). A person with the CFTR ΔF508 mutation will produce an abnormal CFTR protein that lacks this phenylalanine residue and which cannot fold properly. This protein does not escape the endoplasmic reticulum for further processing. Having two copies of this mutation (one inherited from each parent) is the most common cause of cystic fibrosis, responsible for nearly two-thirds of cases worldwide.

Cells were seeded at liquid/liquid interface at 250,000 per insert in modified Lonza medium until confluency was achieved, and then cultures were maintained in 2 mL basolateral medium at Air Liquid Interface (ALI) until fully differentiated. Cultures were washed with Dulbecco's phosphate buffered saline (DPBS) every 48-72 hours. Cells were apportioned in a blind study into treatment and control groups. The compositions were coded and stored at 4° C. until testing. Medium, PBS, and compounds were allowed to come to room temperature prior to application to cultures.

Collected and Stored Biologicals

Apical mucus was collected on ice after 48 hours of accumulation (prior to exposure to treatment or control) in cohorts (on day 15, 22, and 29) and stored at −80° C. Briefly, individual cultures were bathed in 110 μL of 1×DPBS at 37° C. for 20 minutes. Apical mucus was pooled from 4 inserts (100 μL each) into tubes for each of 4 concentration to be tested (control, composition 1, composition 2, and composition 3) and 4 treatment groups (-Lumacaftor (VX-809)/-supernatant from mucopurulent material (SMM), −VX-809/+SMM, +VX-809/−SMM, and +VX-809/+SMM). Samples corresponded to assigned treatment groups.

Basolateral medium (200 μL of 2 mL) was sampled from each insert and stored as pooled cohorts of N=4 for the 16 treatment groups. Samples were taken prior to inflammation, following an 8 hour period of inflammation but prior to treatment, and following 8 hours of inflammation plus 24 hour of treatment. Samples were collected on ice and stored at −80° C.

Treatment

Inflammation: supernatant from mucopurulent material (SMM) from mixed donors was diluted 1:3 in 0.9% saline and 20 μL was applied to the apical surface of cultures (N=32). Non-inflamed cultures (N=32) were treated apically with 20 μL of 0.9% saline alone. The total incubation time was 8 hours.

Compound testing: Pre-inflamed and control cultures were treated apically with 20 μL control, composition 1, composition 2, or composition 3 for 24 hours, and simultaneously with Lumacaftor (VX-809) (5 μM) or DMSO (0.05%) vehicle control in 2 mL of basolateral medium. The experimental design is depicted in FIG. 1. A 0.9% saline solution or supernatant from mucopurulent material (SMM) diluted 1:3 in 0.9% saline, was applied to the apical surface of cultures for 8 hours. Treatment for 24 hours with 20 μL of the composition was applied apically, while simultaneously treating basolaterally with VX-809 (5 μM) or DMSO (0.05%) Ussing experiments were run in two day groupings (1-4) and (5-8). Following bioelectric assessment, cultures were submerged in 300 μL Trizol reagent for RNA isolation and cytokine evaluation.

Bioelectric Measurements

Ussing chamber experiments were performed in bilateral Kreb's bicarbonate ringers solution, bubbled with 5% $CO_2$ at 36° C.±1° C. All chambers were zeroed prior to sample loading. Potential difference (PD) measurements were recorded under open-circuit conditions. Under voltage-clamped conditions, resistance (Rt) and basal current (Isc) was recorded as reference measurements. Short-circuit current (Isc) measurements were acquired every 20 seconds by Acqualize and Analyze software. Inhibitors and agonists were added to the chambers as follows: amiloride (100 μM apical), forskolin (10 μM bilateral), $CFTR_{inh}172$ (10 μM apical), UTP (100 μM apical). Data was exported and processed with Microsoft Excel and Origin software. All data is presented as a Δ mean value ($\mu A/cm^2$)±SEM. Statistical analysis was performed using a two-tailed student's t-Test, assuming equal variance.

Figure 2A:
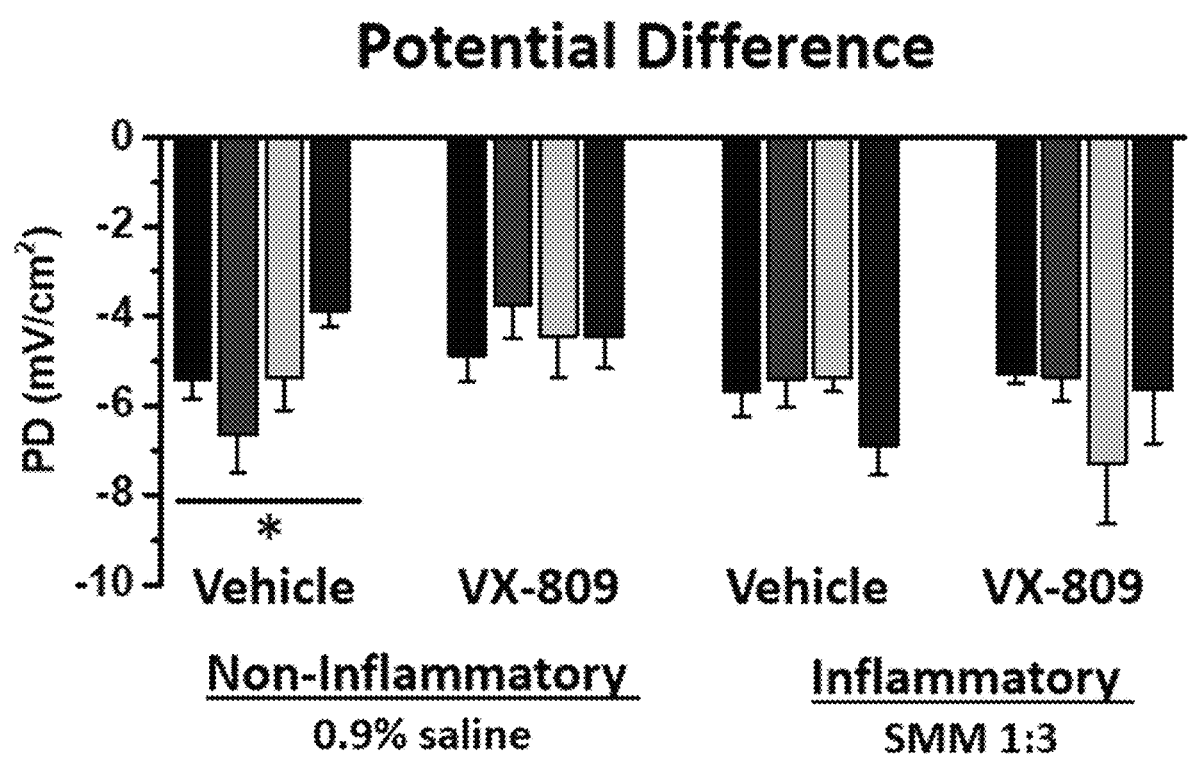
FIGS. 2A-2C depict basal characteristics of cell cultures treated with compositions described herein.
Figure 2B:
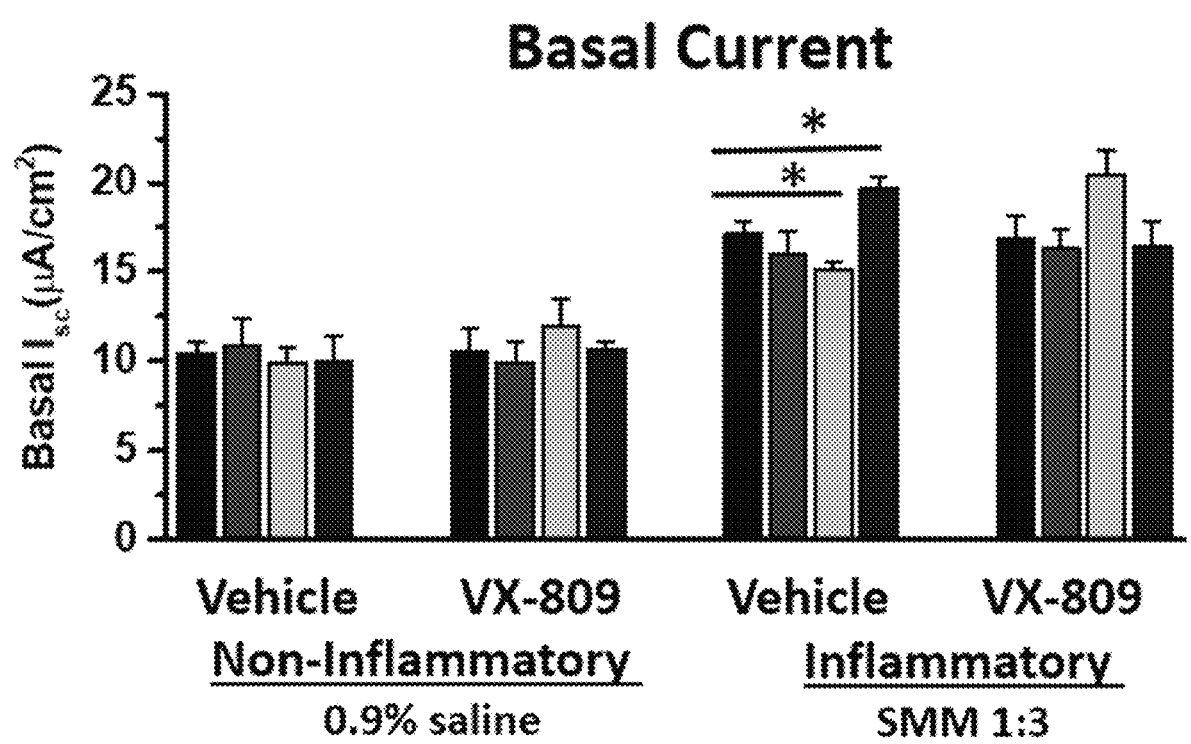
Figure 2C:
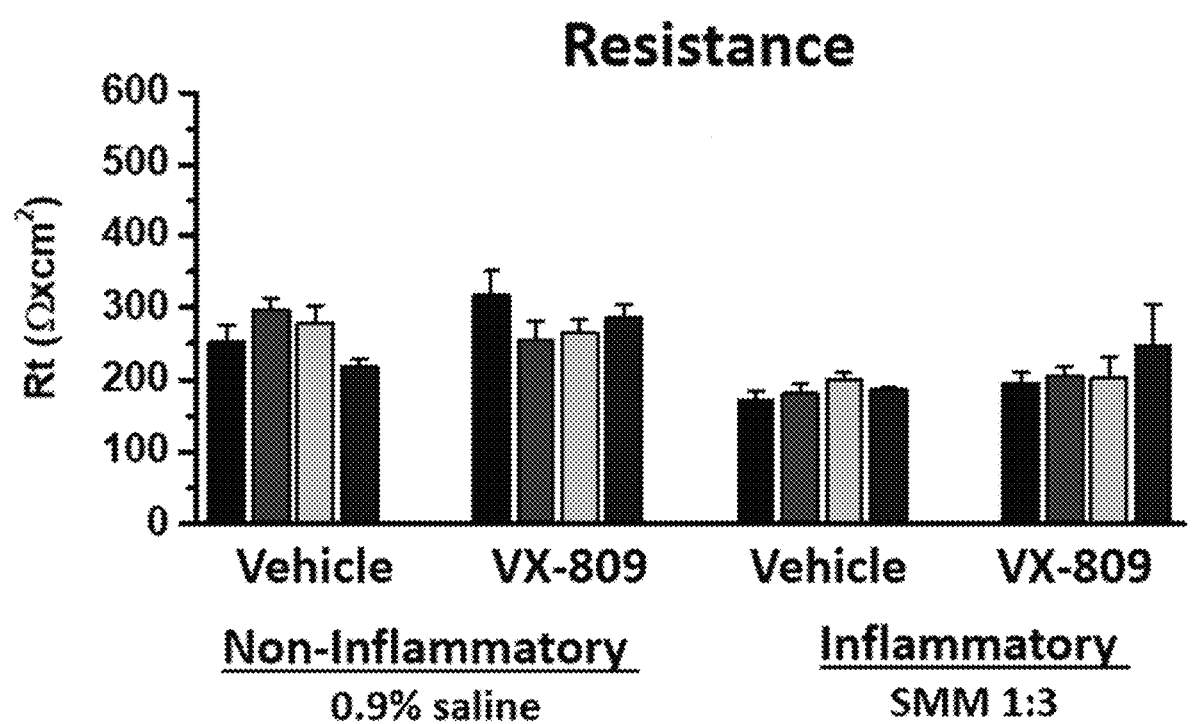

Basal characteristics of cell cultures are shown in FIGS. 2A-2C. The bar graphs are shown in groups of four, with each bar representing treatment with (from left to right): control, composition 1, composition 2, and composition 3. As shown in FIG. 2A, in uninflamed, 0.9% saline-treated cultures, composition 3 treatment resulted in a 1.4 fold reduction in the measured potential difference compared to treatment with control (p=0.0336, two-tailed student's t-test) suggesting that the concentration of composition 3 may have a negative effect on the resting ion channel gradient. As shown in FIG. 2B, under inflammatory conditions, basal current varied to some degree both in the vehicle- and VX-809-treated cultures. The inflammatory conditions affected the basal Isc to varying degrees; composition 2 decreased (p=0.0459), while composition 3 increased basal Isc measurements (p=0.04227) without affecting Resistance values (FIG. 2C). All potential difference, basal current, and resistance values were within normal parameters.

Figure 3A:
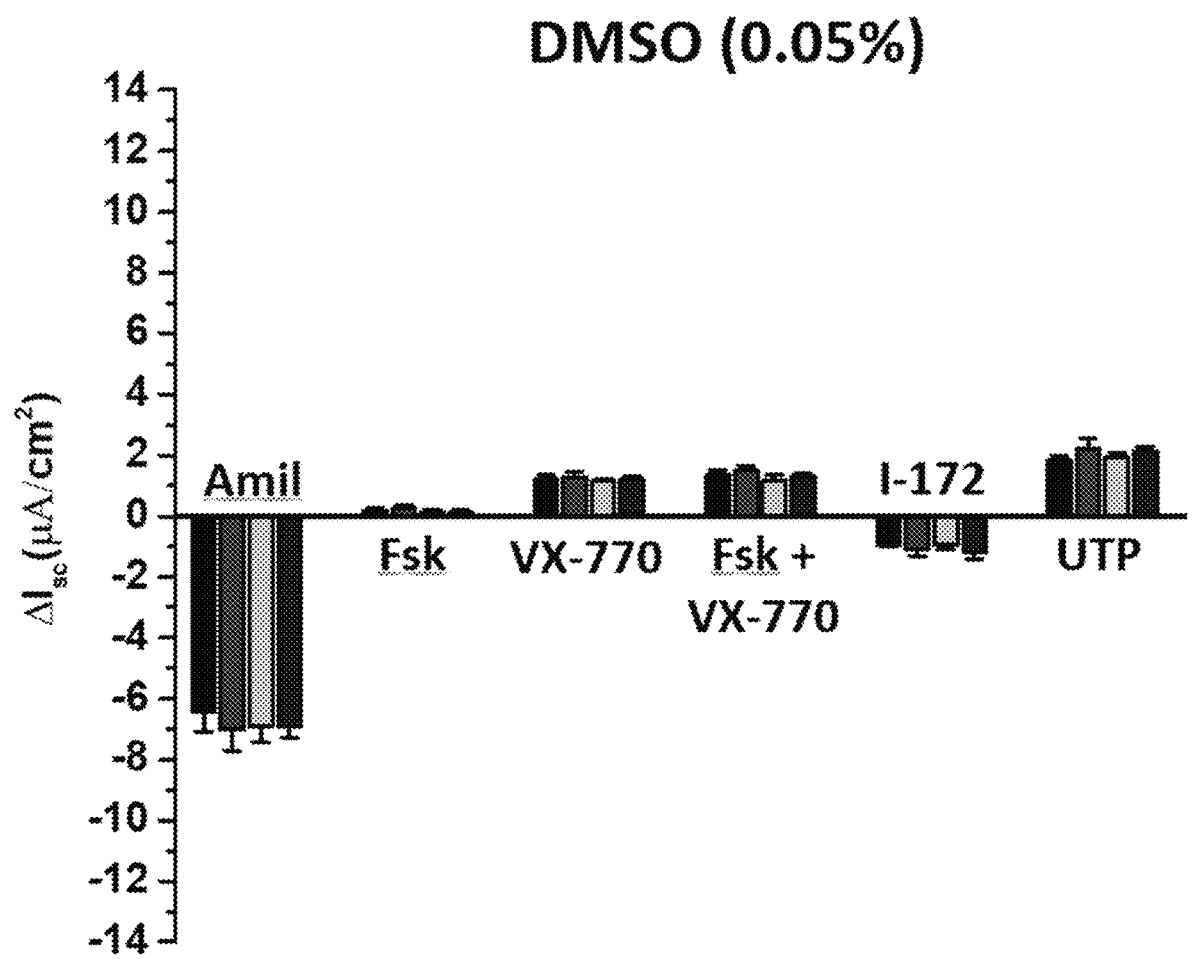
FIGS. 3A-3B show results of Ussing chamber studies in non-inflammatory conditions.
Figure 3B:
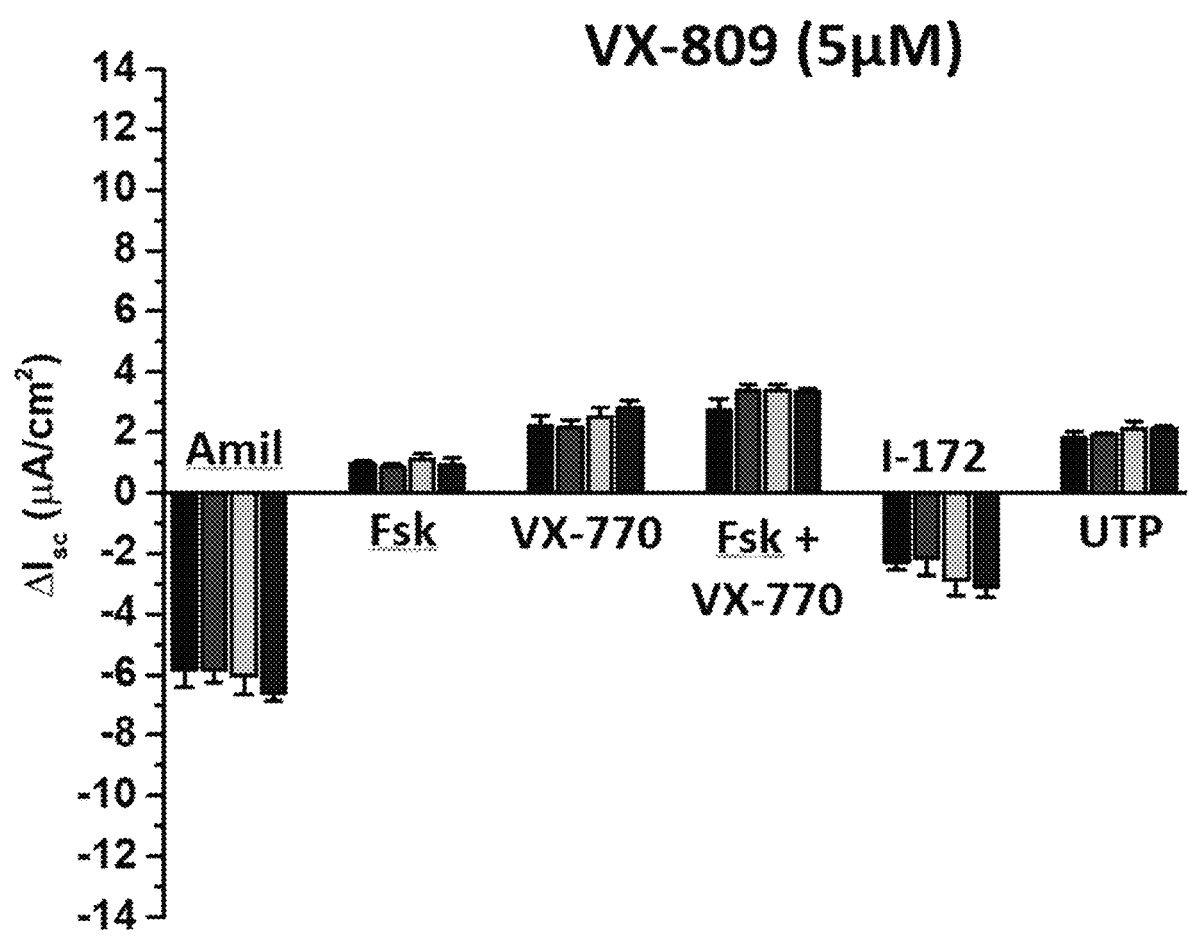

Ussing chamber studies showing ion channel responses under non-inflammatory conditions are shown in FIGS. 3A and 3B. Under non-inflammatory, uncorrected conditions (FIG. 3A), the test compounds did not have a significant effect on ion transport properties when exposed to amiloride (ENaC), forskolin or VX-770 (CFTR), or UTP (CaCC). In non-inflammatory, VX-809-corrected cultures (FIG. 3B), there was no significant difference in the change in current when exposed to amiloride or in forskolin-stimulated Isc when cultures were exposed to the test compounds. An increase in VX-770 potentiated current compared to the control, however the differences were not significant. The maximum response to Fsk+VX770 increased when exposed to compositions 1, 2, and 3 compared to the control. Response to UTP internal control was similar in uncorrected and corrected groups, but was not responsive to the treatment compositions.

Figure 4A:
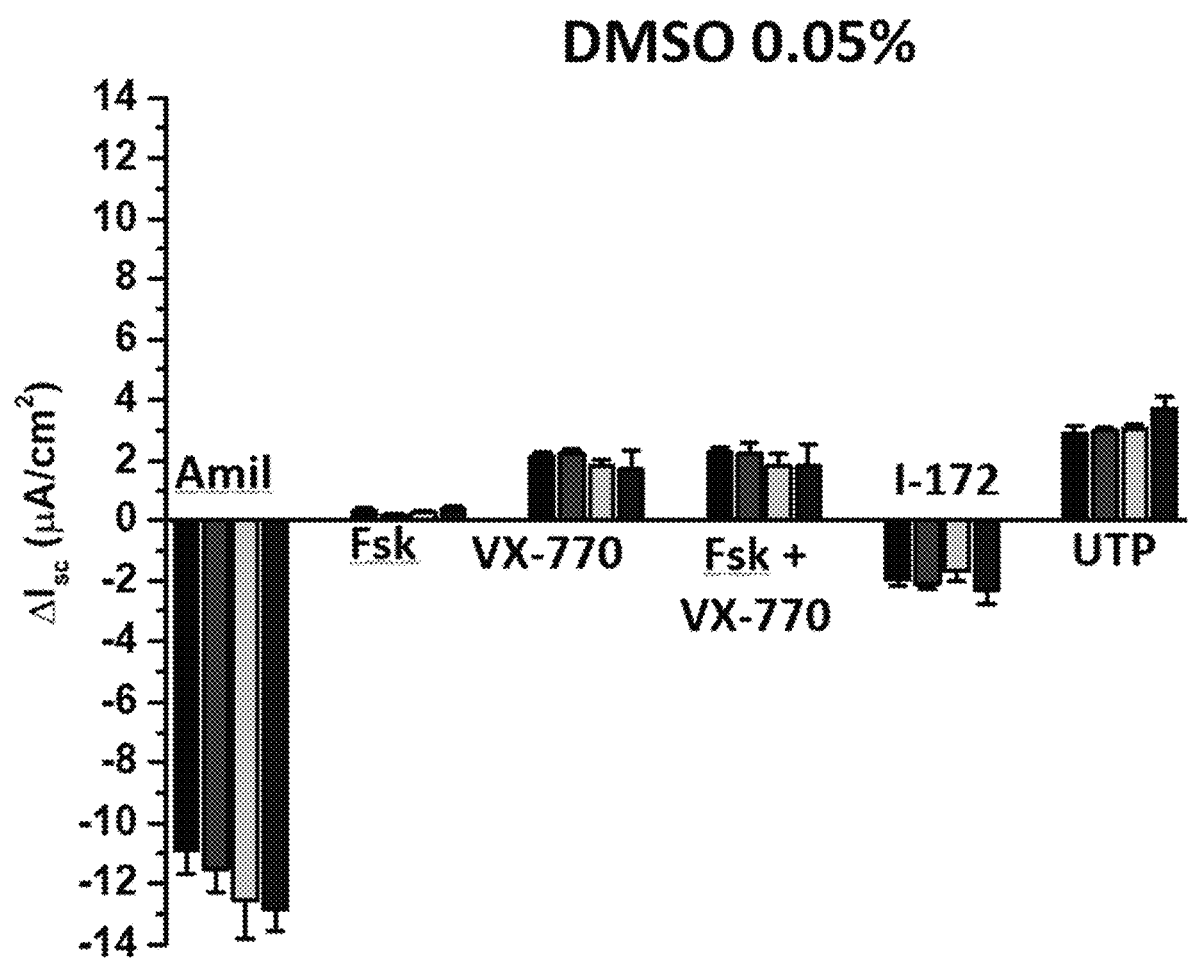
FIGS. 4A-4B show results of Ussing chamber studies in inflammatory conditions.
Figure 4B:
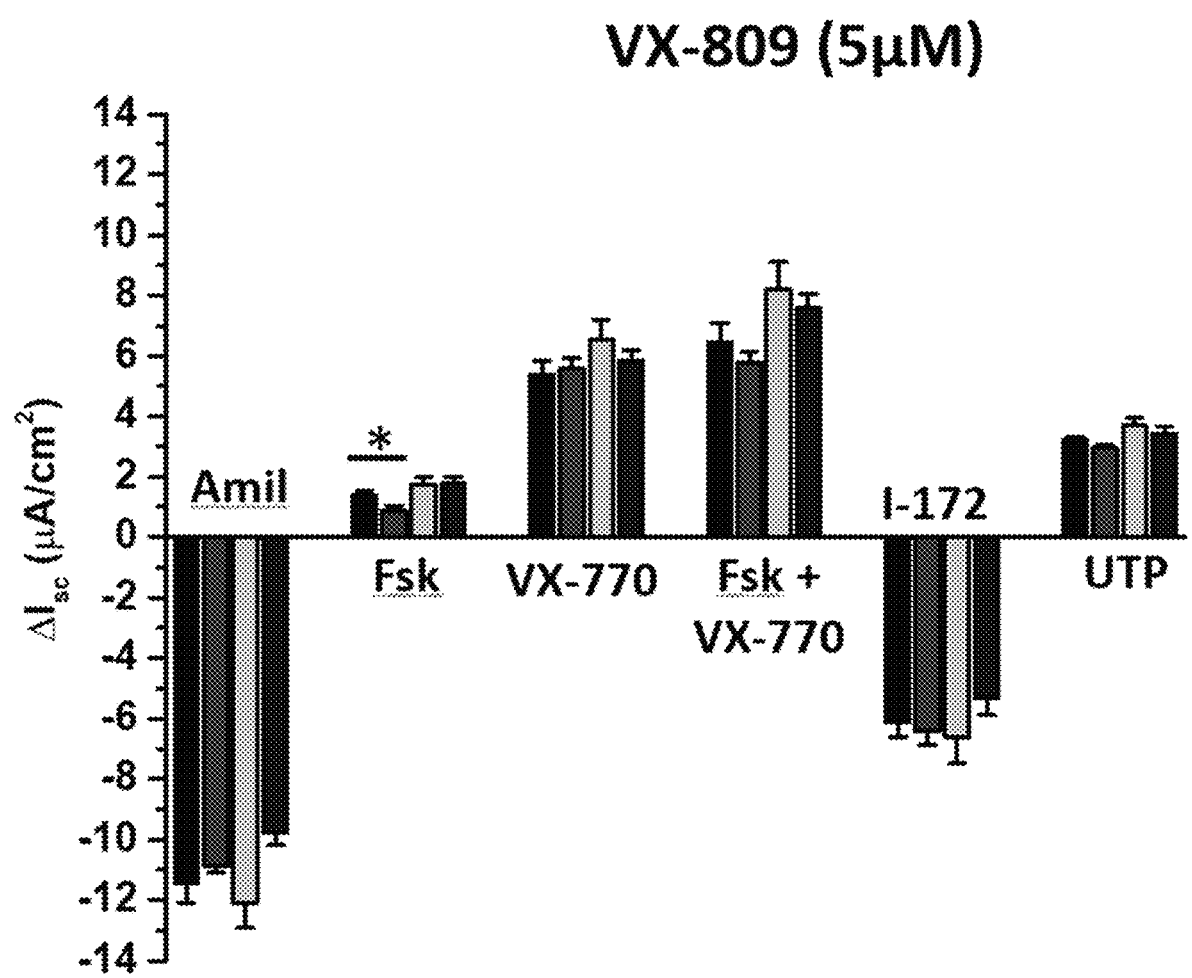

Ussing chamber studies showing ion channel responses under inflammatory conditions are shown in FIGS. 4A and 4B. Under inflammatory conditions, an increase in ENaC response to amiloride was observed compared to non-inflamed cultures, regardless of the treatment group, demonstrating one of the effects of SMM alone. Although the forskolin responses were minimal even after VX-809 correction in inflamed cultures, a decrease in forskolin mediated stimulation in response to composition 1 (p=0.0430) was observed compared to the control. The small forskolin responses overall are likely donor-specific, and not conclusively a result of action by composition 1.

Figure 5A:
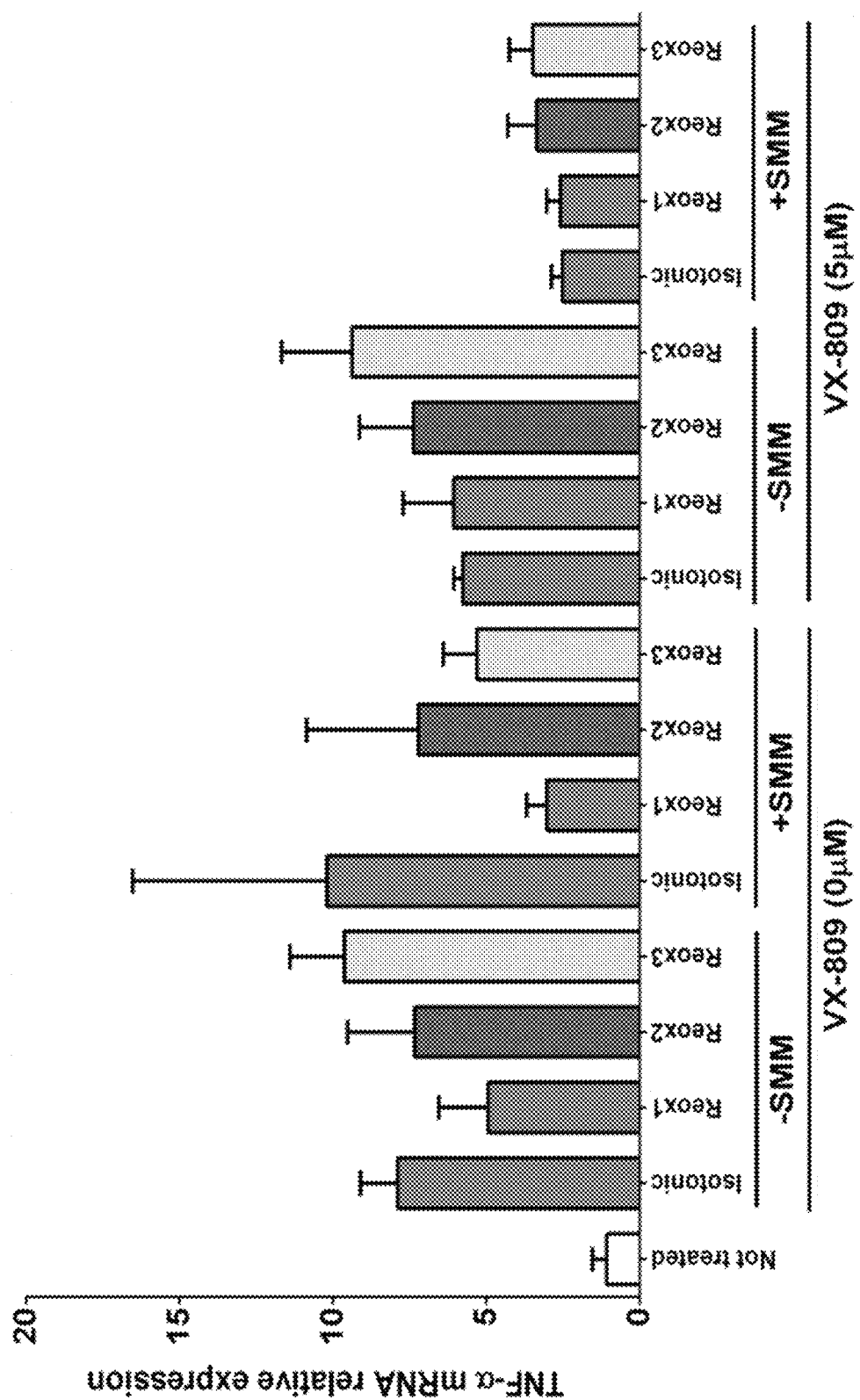
FIGS. 5A-5B show results of reverse transcription polymerase chain reaction (RT-PCR) analysis of IL-8 and TNFα mRNA levels in cells cultures treated with various compositions (as indicated on the x-axis), and with basal conditions (−SMM) or inflammatory conditions (+SMM).
Figure 5B:
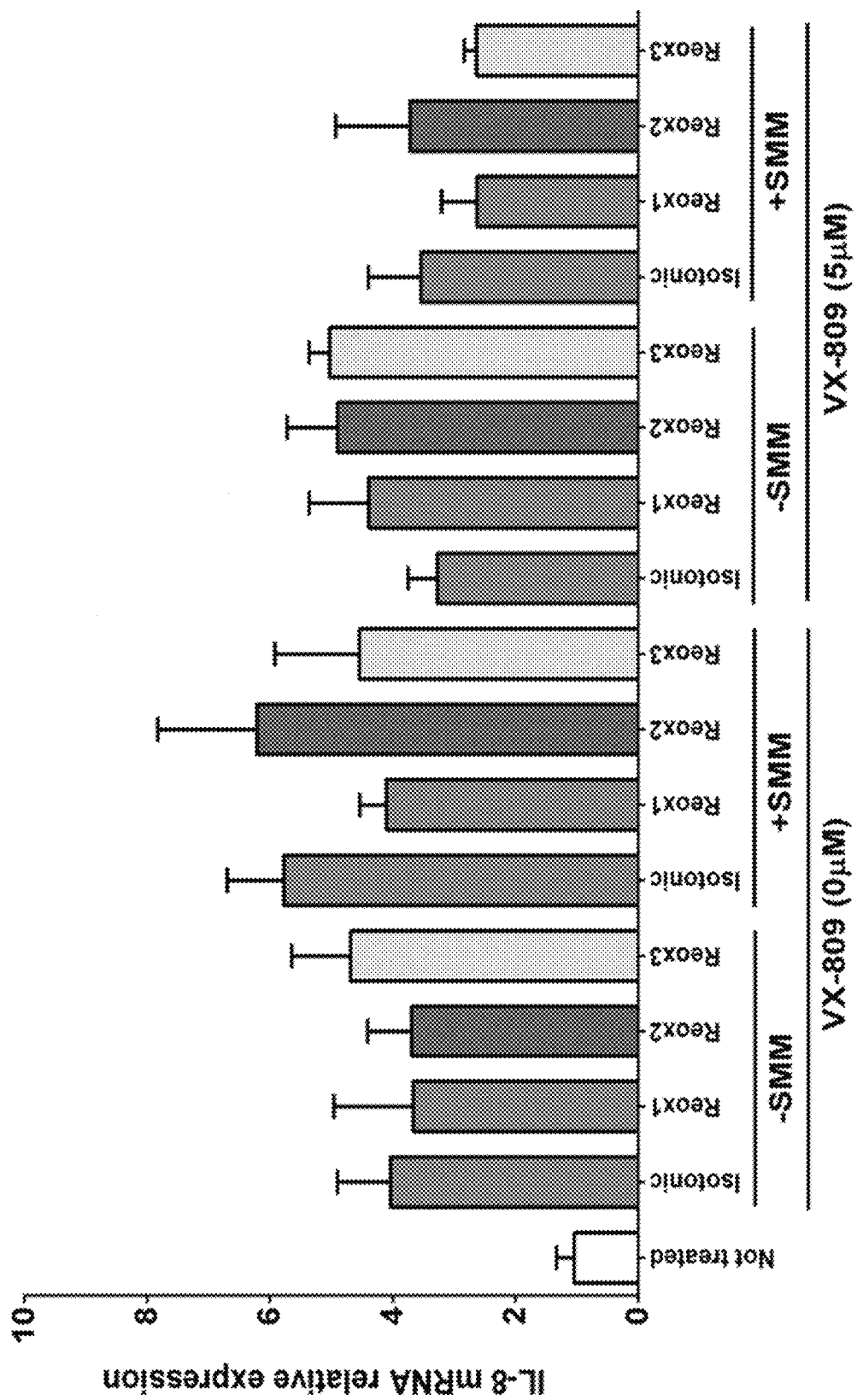
Figure 6A:
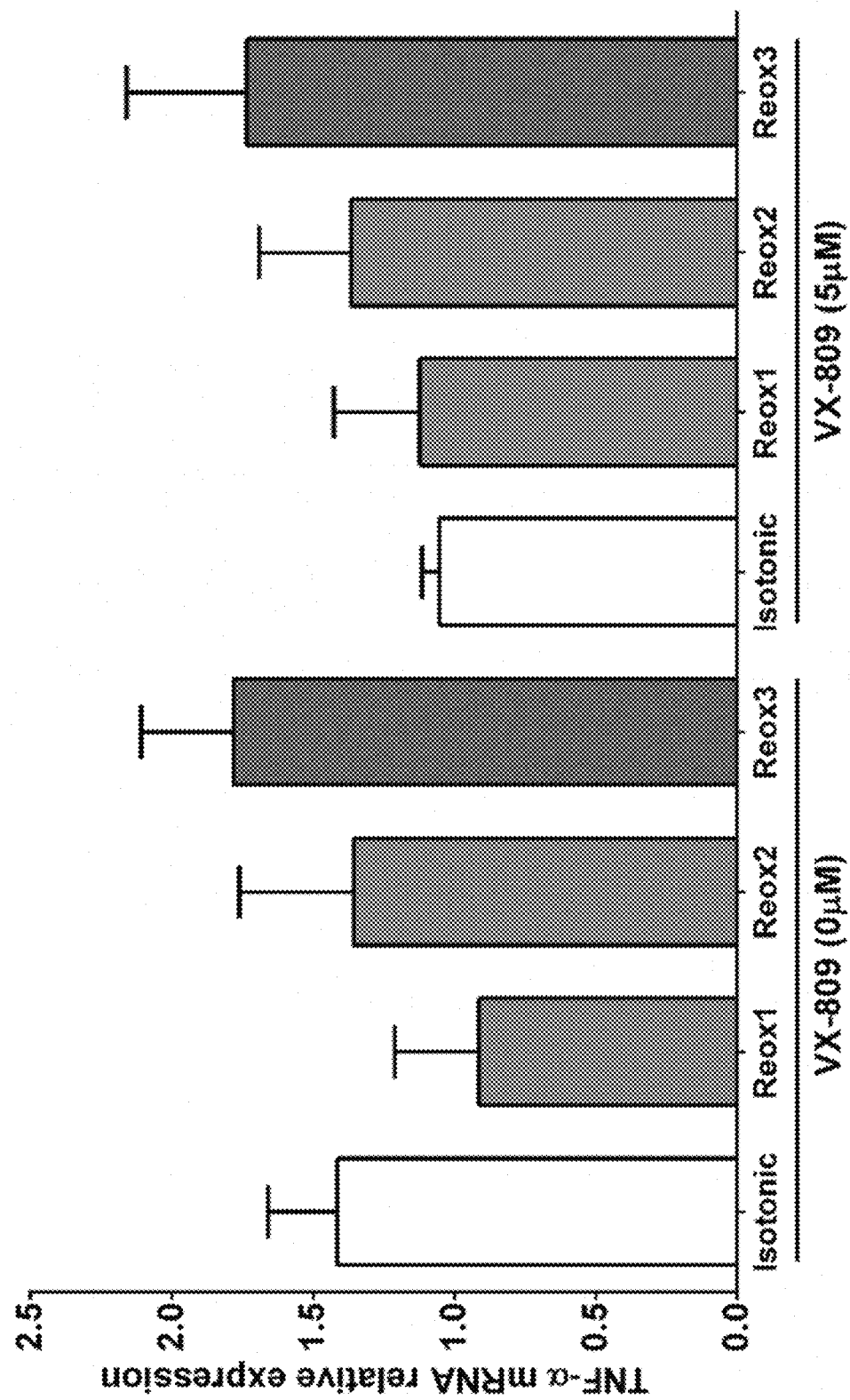
FIGS. 6A-6B show results of RT-PCR analysis of IL-8 and TNFα mRNA levels in the absence of SMM (under basal conditions).
Figure 6B:
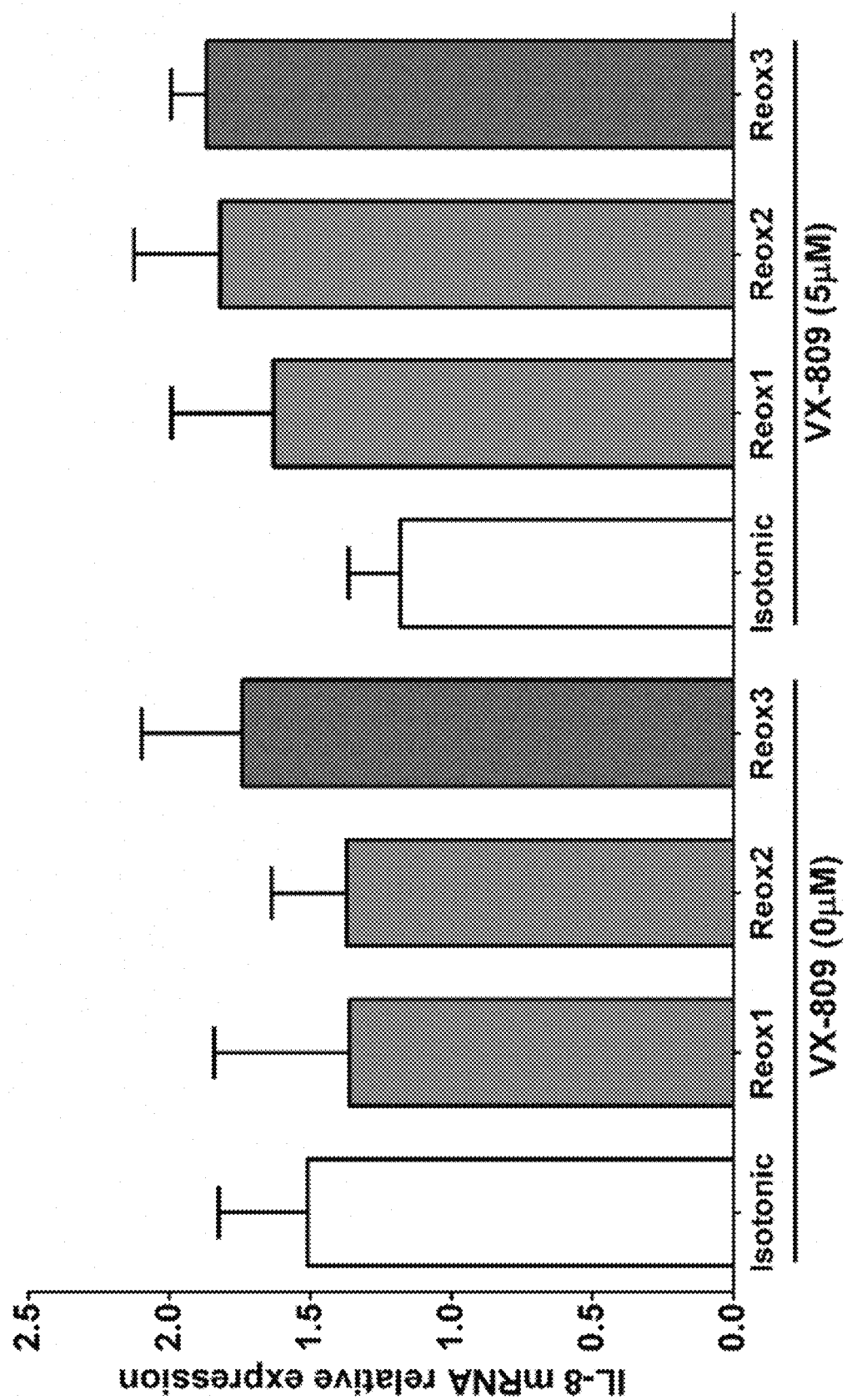
Figure 7A:
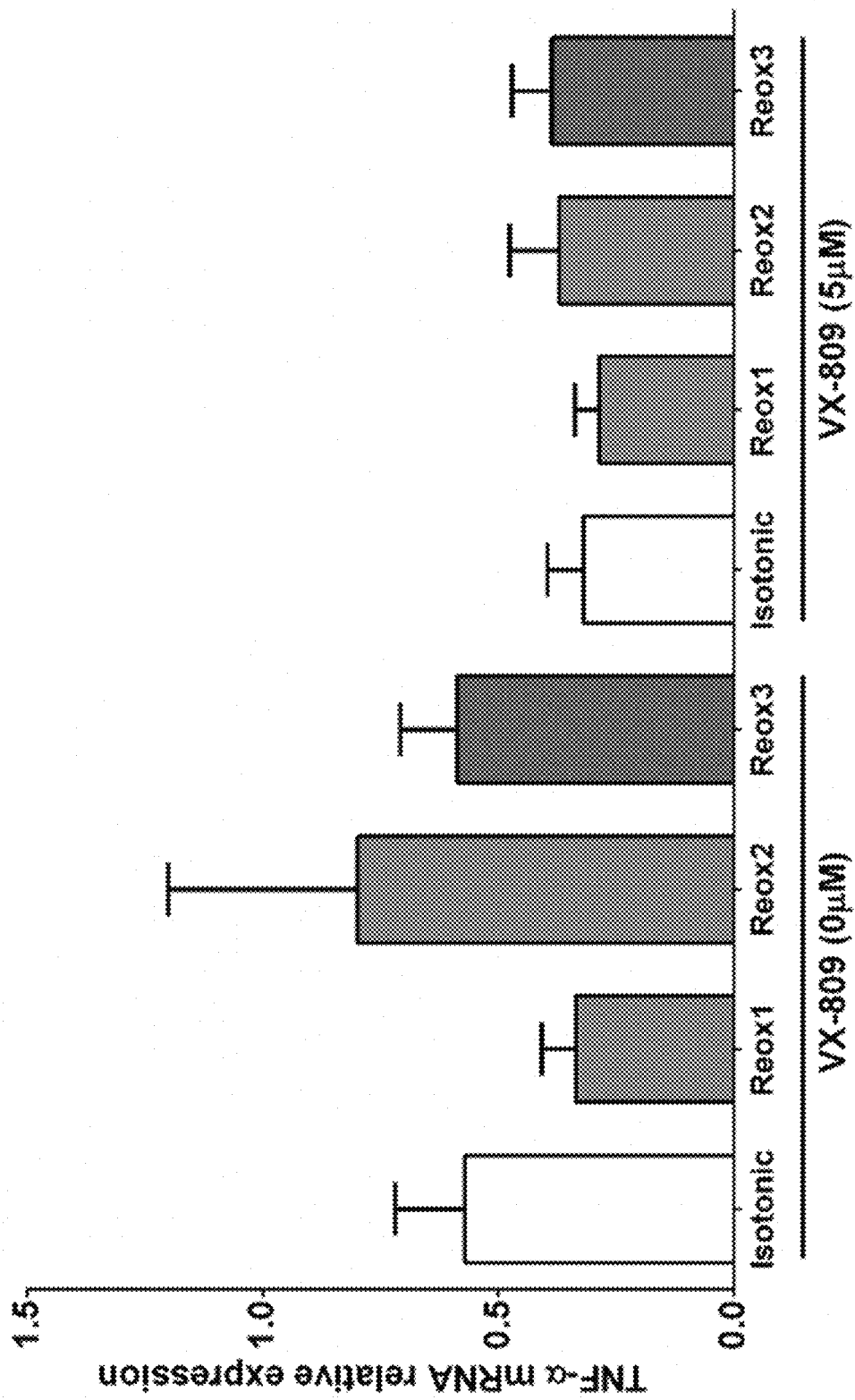
FIGS. 7A-7B show results of RT-PCR analysis of IL-8 and TNFα mRNA levels in the presence of SMM (under inflammatory conditions).
Figure 7B:
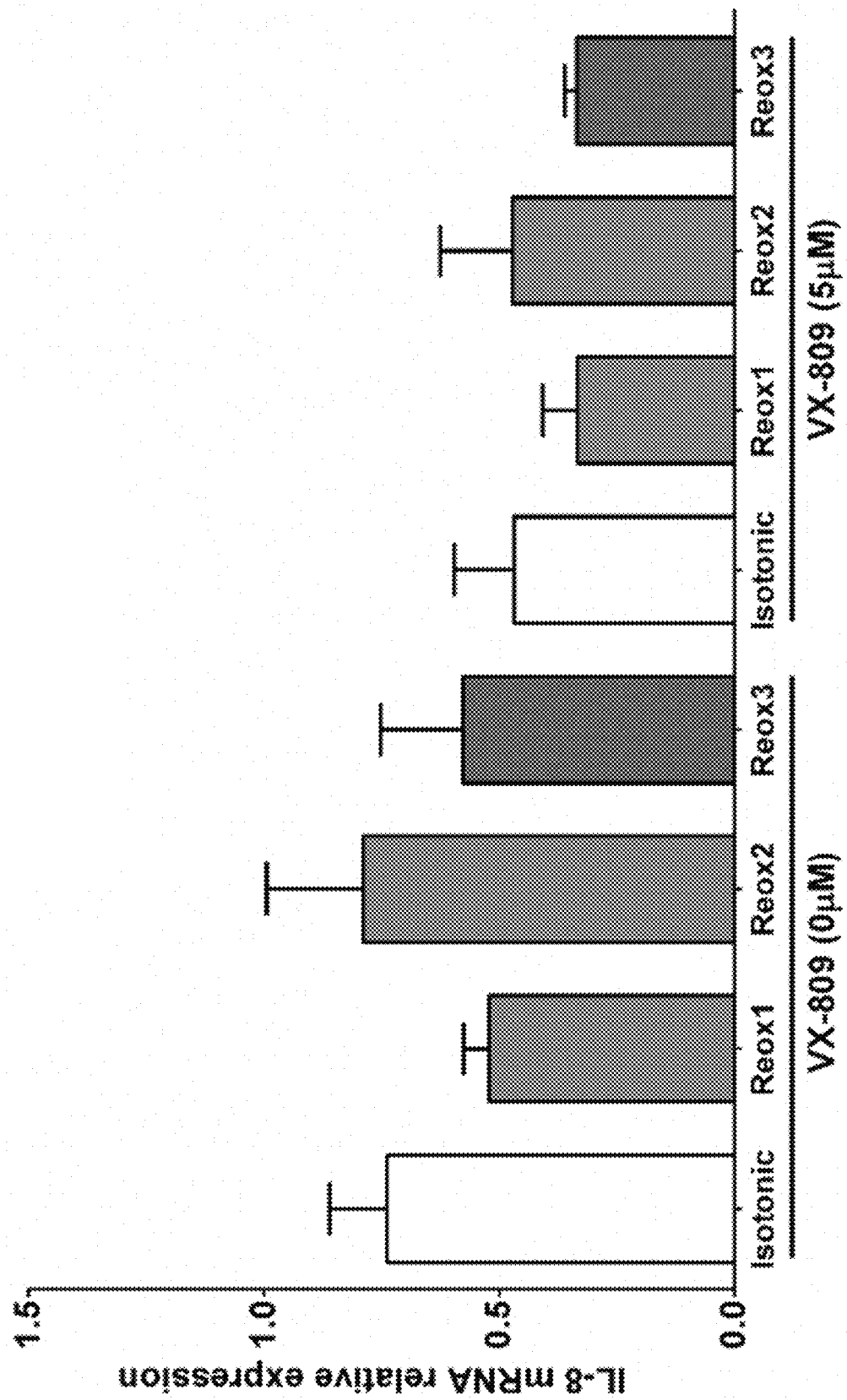
Figure 8A:
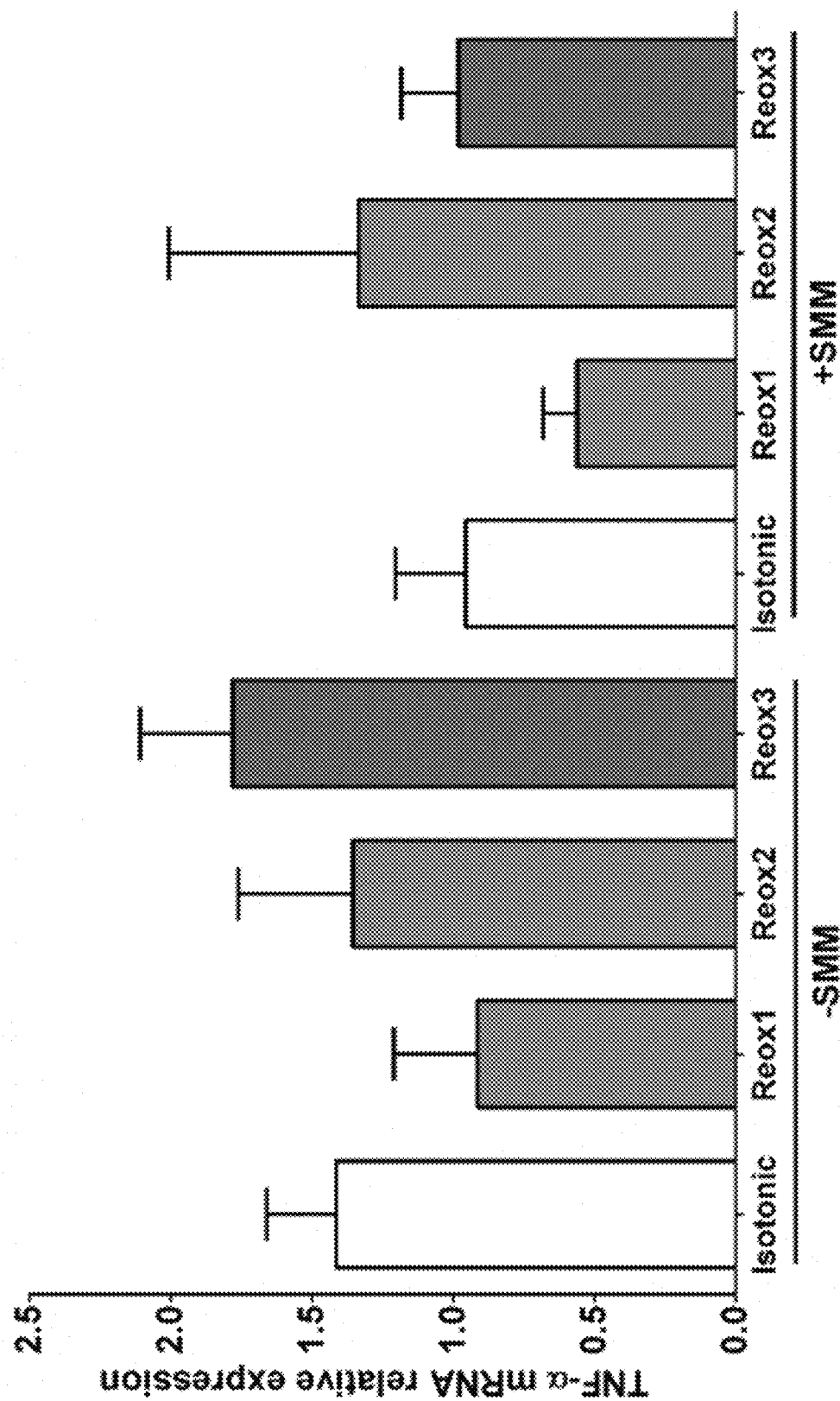
FIGS. 8A-8B show results of RT-PCR analysis of IL-8 and TNFα mRNA levels under control conditions (treated with vehicle).
Figure 8B:
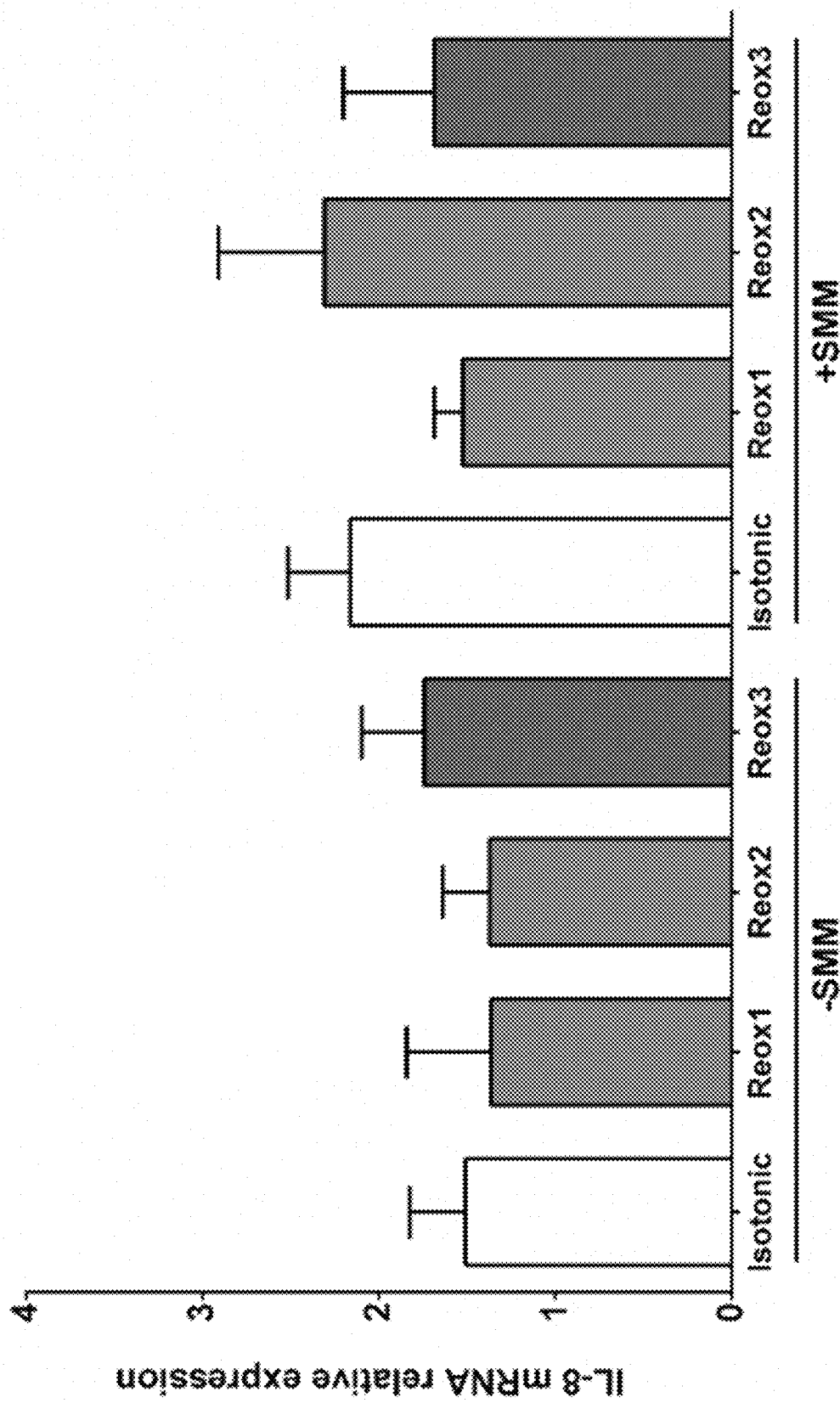
Figure 9A:
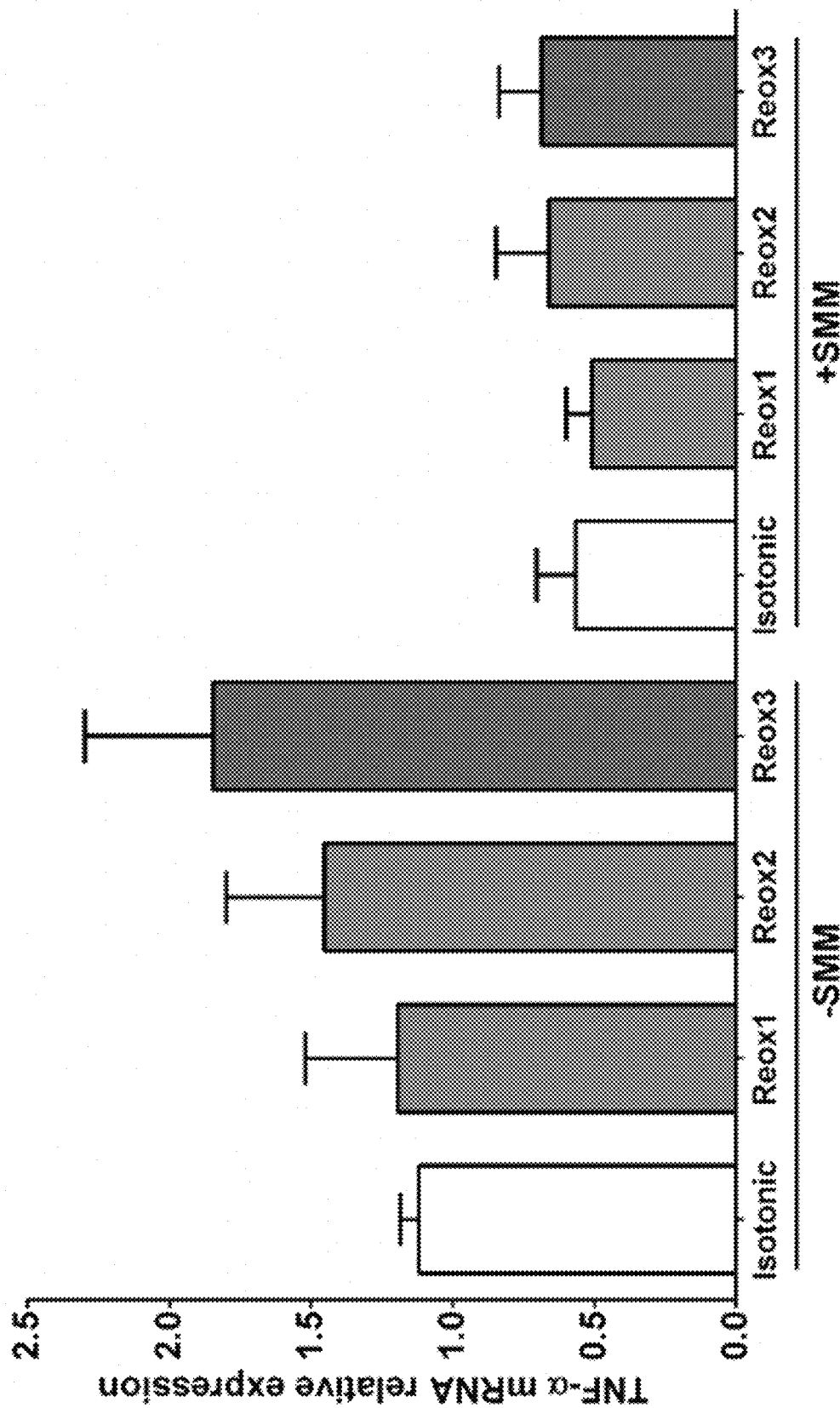
FIGS. 9A-9B show results of RT-PCR analysis of IL-8 and TNFα mRNA levels in the presence of VX-809.
Figure 9B:
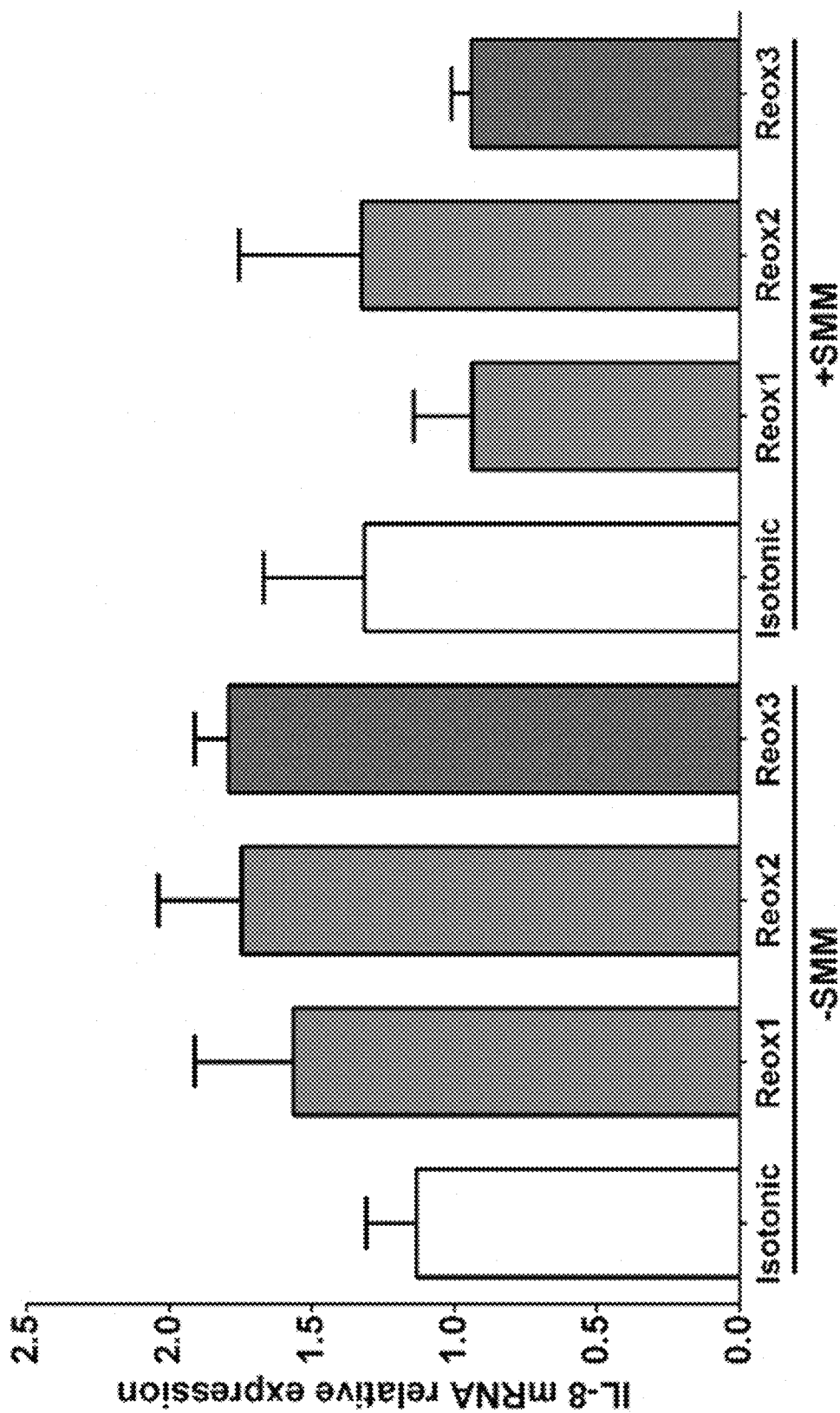

RT-PCR analysis was performed to analyze TNFα and IL-8 mRNA expression levels. As shown in FIGS. 5A and 5B, vehicle ("isotonic condition") with or without the treatment compositions increased the mRNA levels of TNF-α and IL-8 under basal (−MM) or under inflammatory (+SMM) conditions (compared with not-treated, naïve cultures). Under basal conditions, in the absence of SMM, treatment with the treatment compositions did not decrease the mRNA levels of TNFα and IL-8 in presence or absence of VX-809 (FIGS. 6A and 6B). Under inflammatory conditions (+SMM), treatment with the treatment compositions did not decrease the mRNA levels of TNFα and IL-8 in presence or absence of VX-809 (FIGS. 7A and 7B). Under vehicle-treated conditions (used for VX-809), treatment with the treatment compositions did not decrease the mRNA levels of TNFα and IL-8 in presence or absence of SMM (FIGS. 8A and 8B). Under VX-809-treated conditions, treatment compositions did not decrease the mRNA levels of TNFα and IL-8 in the presence or absence of SMM (FIGS. 9A and 9B). Levels of TNFα and IL-8 mRNA were determined by quantitative RT-PCR and expressed as fold change to 18S mRNA. All treatments were compared to non-treated cells.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for treating a pulmonary infection in a subject, comprising:
  administering to the subject a composition comprising:
    0.9% saline solution; and
    75 ppm hypochlorite,
  wherein the saline solution comprises a salt, the salt comprising:
    aluminum in an amount of about 103 ppm to about 126 ppm,
    bromine in an amount of about 50 ppm to about 62 ppm,
    calcium in an amount of about 1891 ppm to about 2311 ppm,
    iron in an amount of about 74 ppm to about 90 ppm,
    magnesium in an amount of about 1750 ppm to about 2138 ppm,
    phosphorus in an amount of about 4.6 ppm to about 5.6 ppm,
    potassium in an amount of about 1555 ppm to about 1901 ppm, and
    strontium in an amount of about 29 ppm to about 35 ppm; and,
  wherein the composition is administered in an amount sufficient to treat the pulmonary infection in the subject.

2. The method of claim 1, further comprising administering an antibiotic agent, an anti-inflammatory agent, a bronchodilator, a mucolytic agent, or oxygen therapy to the subject.

3. The method of claim 1, further comprising administering ivacaftor, lumacaftor, tezacaftor, or analogues, derivatives, or combinations thereof to the subject.

4. The method of claim 1, wherein the composition is administered intranasally or by inhalation.

5. The method of claim 1, further comprising reducing the presence of an infectious organism in the lung.

6. The method of claim 5, wherein the infectious organism is *Pseudomonas aeruginosa* or *Burkholderia cepacia*.

7. The method of claim 5, wherein reducing the presence of an infectious organism reduces a dependency on or use of an antibiotic therapy.

8. The method of claim 7, wherein the antibiotic therapy is erythromycin, tobramycin, or vancomycin.

9. The method of claim 1, further comprising reducing mucus viscosity.

10. The method of claim 9, wherein reducing mucus viscosity clears mucus buildup.

11. The method of claim 9, further comprising promoting oxidation of nucleic acid material and oxidation of trapped organic materials.

12. The method of claim 9, wherein reducing mucus viscosity reduces a dependency on or use of a mucolytic agent.

13. The method of claim 12, wherein the mucolytic agent is dornase alfa, denufosol, acetylcysteine, hypertonic saline, or ambroxol.

14. The method of claim 1, further comprising enhancing cystic fibrosis transmembrane conductance regulator (CFTR) function in a lung, wherein enhancing CFTR function maintains a surface liquid interface required for proper cilia function.

15. The method of claim 1, further comprising reducing lung inflammation.

16. The method of claim 15, wherein reducing lung inflammation reduces the use of non-steroidal anti-inflammatory drugs (NSAIDs).

17. The method of claim 1, further comprising generating nitric oxide in blood vessels.

18. The method of claim 17, wherein generating nitric oxide stimulates endothelial nitric-oxide synthesis (NOS).

19. A method for treating a pulmonary infection in a subject, comprising:
   administering to the subject an electrolyzed saline solution, the electrolyzed saline comprising a reactive oxygen species and a salt present in an amount of about 0.01% to about 1%, the salt comprising:
      aluminum in an amount of about 103 ppm to about 126 ppm,
      bromine in an amount of about 50 ppm to about 62 ppm,
      calcium in an amount of about 1891 ppm to about 2311 ppm,
      iron in an amount of about 74 ppm to about 90 ppm,
      magnesium in an amount of about 1750 ppm to about 2138 ppm,
      phosphorus in an amount of about 4.6 ppm to about 5.6 ppm,
      potassium in an amount of about 1555 ppm to about 1901 ppm,
      and strontium in an amount of about 29 ppm to about 35 ppm; and;
   wherein the composition is administered in an amount sufficient to treat the pulmonary infection in the subject.

20. The method of claim 19, wherein the reactive oxygen species comprises hypochlorite present in an amount of about 4 ppm to about 100 ppm.

* * * * *